(12) United States Patent
Albisser et al.

(10) Patent No.: US 8,768,673 B2
(45) Date of Patent: Jul. 1, 2014

(54) COMPUTER-IMPLEMENTED SYSTEM AND METHOD FOR IMPROVING GLUCOSE MANAGEMENT THROUGH CLOUD-BASED MODELING OF CIRCADIAN PROFILES

(75) Inventors: Anthony Michael Albisser, The Villages, FL (US); Lucienne Marie Ide, Coral Gables, FL (US)

(73) Assignee: Rimidi Diabetes, Inc., Atlanta, GA (US)

( * ) Notice: Subject to any disclaimer, the term of this patent is extended or adjusted under 35 U.S.C. 154(b) by 77 days.

(21) Appl. No.: 13/559,547

(22) Filed: Jul. 26, 2012

(65) Prior Publication Data
US 2014/0032194 A1    Jan. 30, 2014

(51) Int. Cl.
- G06G 7/48 (2006.01)
- G06G 7/58 (2006.01)
- G01N 33/48 (2006.01)
- G01N 31/00 (2006.01)

(52) U.S. Cl.
USPC .................... 703/11; 703/12; 702/19; 702/22

(58) Field of Classification Search
None
See application file for complete search history.

(56) References Cited

U.S. PATENT DOCUMENTS

| | | | |
|---|---|---|---|
| 5,822,715 A | 10/1998 | Worthington et al. |
| 6,024,699 A | 2/2000 | Surwit et al. |
| 6,168,563 B1 | 1/2001 | Brown |
| 6,421,633 B1 | 7/2002 | Heinonen et al. |
| 6,544,212 B2 | 4/2003 | Galley et al. |
| 6,925,393 B1 | 8/2005 | Kalaz et al. |
| 7,025,425 B2 | 4/2006 | Kovatchev et al. |
| 7,137,951 B2 | 11/2006 | Pilarski |
| 7,167,818 B2 | 1/2007 | Brown |
| 7,282,029 B1 | 10/2007 | Poulsen et al. |
| 7,311,666 B2 | 12/2007 | Stupp et al. |
| 7,353,152 B2 | 4/2008 | Brazhnik et al. |
| 7,356,423 B2 | 4/2008 | Nehrig |

(Continued)

FOREIGN PATENT DOCUMENTS

| | | |
|---|---|---|
| EP | 834825 | 4/1998 |
| EP | 881495 | 12/1998 |

(Continued)

OTHER PUBLICATIONS

Tudor et al. (Computer Methods and Programs in Biomedicine, 1998, 56, 175-192).*

(Continued)

*Primary Examiner* — Larry D Riggs, II
(74) *Attorney, Agent, or Firm* — Patrick J. S. Inouye; Makiko Coffland

(57) ABSTRACT

A computer-implemented system and method for improving glucose management through cloud-based modeling of circadian profiles is provided. For each daily meal period, two sets of pre- and post-meal period data that include a blood glucose level and a diabetes medication dosing are stored into a circadian profile for a diabetic patient in a cloud computing infrastructure. Predicted blood glucose is modeled over the infrastructure and the access will be validated. A model, including expected blood glucose values and their predicted errors is created from the blood glucose levels in each profile and visualized in a log-normal distribution. Target ranges for blood glucose are determined and superimposed over the expected values. Pharmacodynamics of the medication are obtained. An incremental change in dosing of the medication is propagated over a model day and the expected blood glucose values and their predicted errors are adjusted in response to the incremental dosing change.

22 Claims, 11 Drawing Sheets

(56) References Cited

U.S. PATENT DOCUMENTS

| | | |
|---|---|---|
| 7,404,796 B2 | 7/2008 | Ginsberg |
| 7,651,845 B2 | 1/2010 | Doyle et al. |
| 7,824,333 B2 | 11/2010 | Otto et al. |
| 2001/0011224 A1 | 8/2001 | Brown |
| 2001/0047252 A1 | 11/2001 | Brown |
| 2002/0022773 A1 | 2/2002 | Drinan et al. |
| 2003/0208113 A1 | 11/2003 | Mault et al. |
| 2005/0071141 A1 | 3/2005 | Butler |
| 2005/0121322 A1 | 6/2005 | Say et al. |
| 2005/0125158 A1 | 6/2005 | Schlessinger et al. |
| 2005/0234311 A1 | 10/2005 | Kouchi et al. |
| 2005/0244910 A1 | 11/2005 | Wolever et al. |
| 2006/0167345 A1 | 7/2006 | Vespasiani |
| 2006/0276771 A1 | 12/2006 | Galley et al. |
| 2007/0149861 A1 | 6/2007 | Crothall et al. |
| 2007/0282177 A1 | 12/2007 | Pilz |
| 2008/0154513 A1 | 6/2008 | Kovaltchev et al. |
| 2008/0234992 A1 | 9/2008 | Ray et al. |
| 2008/0306353 A1 | 12/2008 | Douglas et al. |
| 2009/0006061 A1 | 1/2009 | Thukral et al. |
| 2009/0036753 A1 | 2/2009 | King |
| 2009/0036828 A1 | 2/2009 | Hansen et al. |
| 2009/0164239 A1 | 6/2009 | Hayter et al. |
| 2010/0145174 A1 | 6/2010 | Alferness |
| 2010/0174553 A1 | 7/2010 | Kaufman et al. |
| 2010/0262434 A1 | 10/2010 | Shaya |
| 2011/0196213 A1 | 8/2011 | Thukral et al. |
| 2012/0046966 A1 | 2/2012 | Chang et al. |
| 2012/0172694 A1 | 7/2012 | Desborough et al. |

FOREIGN PATENT DOCUMENTS

| | | |
|---|---|---|
| EP | 1281351 | 2/2003 |
| EP | 2023256 | 2/2009 |
| WO | 01/72208 | 10/2001 |
| WO | 2004/015539 | 2/2004 |
| WO | 2007065285 | 6/2007 |

OTHER PUBLICATIONS

Rodbard, (Journal of Diabetes Science and Technology, 2009, 3(6), 1395-1401).*

Ramgovind et al. (IEEE, Information Security for South Africa, (ISSA), Aug. 2-4, 2010, 1-7).*

Dungan, "1,5 Anhydroglucitol and Postpandrial Hyperglycemia as Measured by Continuous Glucose Monitoring System in Moderately Controlled Patients With Diabetes", Diabetes Care, vol. 29, No. 6, Jun. 2006, 1214-1219.

Kilpatrick et al. "Plasma 1,5 anhydroglucitol concentrations are influenced by variations in the renal threshold for glucose", 1999, Diabetic Medicine, 16, 496-499.

Akanuma et al. "Urinary excretion of 1,5-anhydro-D-glucitolaccompanying glucose excretion in diabetic patients", Diabetologia (1988)31 : 831 835.

Pitkanen, "Mannose, mannitol, fructose and 1,5-anhydroglucitol concentrations measured by gas chromatography/mass spectrometry in blood plasma of diabetic patients", Clinica Chimica Acta 251 (1996) 91-103.

Suzuki et al. "Production of 1,5-anhydroglucitol from 1,5-anhydrofructose in arythroleukemia cells", Eur. J. Biochem. 240, 23-29 (1996).

Yamanouchi et al. "Origin and disposal of 1,5 anhydroglucitol, a major polyol in the human body", Am. J. Physiol. 263 (Endocrinol. Metab. 26): E268-E273, 1992.

Yamanouchi et al. "Reduction of plasma 1,5-anhydroglucitol (1-deoxyglucose) concentration in diabetic patients" Diabetologia, vol. 31, No. 1,1988, p. 41-45.

Yamanouchi et al. "1,5-Anhydroglucitol stimulates insulin relase in insulinoma cell lines", Biochimica et Biophysica Acta 1623 (2003) 82-87.

Frohnauer et al. "Graphical Human-Insulin time-Activity Profiles Using Standardized Definitions" Diabetes Technology and Therapeutics; vol. 3, No. 3, 2001, p. 419-429.

Perez-Martin et al. Simplified Measurement of Insulin Sensitivity with the Minimal Model Procedure in Type 2 diabetic patients without measurements of insulinemia, Horm Metab Research, 2002; 34:102-106.

O'Leary et al., "Exercise-Induced reversal of Insulin Resistance in Obese Elderly Is Associated With Reduced Visceral Fat," J Appl Physiol 100: 1584-1589, 2006.

K. W. Beach, "A Theoretical Model to Predict the Behavior of Glycosylated Hemoglobin Levels," Journal of Theoretical Biology, Academic Press Inc, London, pp. 547-561 (Jan. 1, 1979).

H. E. Levobitz, "Insulin Resistance: Definition and Consequences," Exp Clin Endocrinol Diabetes 109, Suppl. 2, pp. S135-S148 (2001).

Park et al., "PDA Based Point of Care Personal Diabetes Management Systems," Proceedings of the 2005 IEEE Engineering in Medicine and Biology 27th Annual Conference, Shanghai, China, Sep. 1-4, 2005, pp. 3749-3752 (Sep. 2005).

D. Mendosa, "On-Line Diabetes Resources, Part 13: Diabetes Management Software," NPL_online_diabetes_resources.pdf, retrieved from internet: < URL: http://mendosa.com/software/ htm>(1995).

Mathworks, "Chapter 3. Interpolation," Feb. 15, 2008 pp. 1-27, retrieved from Internet: <URL: http://www.mathworks.com/moler/interp.pdf>.

Jacobs et al, "Nutrients, foods, and dietary patterns as exposure in research: a framework for food synergy", American Society for Clinical Nutrition, No. 78 (suppl), pp. 508S-513S (2003).

Wolever et al., "Prediction of Glucose and Insulin Responses of Normal Subjects after Consuming Mixed Meals Varying in Energy, Protein, Fat, Carbohydrate and Glycemic Index," The Journal of Nutrition, No. 126, pp. 2807-2812 (1996).

Powell et al., "International Table of Glycemic Index and Glycemic Load Values: 2002," American Society for Clinical Nutrition, No. 76, pp. 5-56 (2002).

Lehmann et al., "An Integrated Approach for the Computer-Assisted Treatment of Diabetes Patients on Insulin," Medical Informatica, Taylor and Francis, Basingstoke, GB, vol. 17, No. 2, Apr. 1, 1992, pp. 105-123 (Apr. 1, 1992).

Salzsieder et al., "A Model-Based System for the Individual Prediction of Metabolic Responses to Improve the Therapy in Type I Diabetes," Hormone and Metabolic Research, Thieme-Stratton, Stuttgart, DE, vol. 24, No. Suppl., Jan. 1, 1990, pp. 10-19 (Jan. 1, 1990).

G. Trevino, "On the Weighted-Average Relationship between Plasma Glucose and HbA1c," Diabetes Care, vol. 29, No. 29, p. 466 (Feb. 2006).

Cely et al., "Relationship of Baseline Glucose Homeostasis to Hyperglycemia during Medical Critical Illness," Chest, No. 126(3), pp. 879-887 (Sep. 2004).

R. Landgraf, "The Relationship of Postprandial Glucose to HbA1c," Diabetes/Metabolism Research and Reviews, No. 20(Suppl 2), pp. S9-S12 (2004).

Chandalia et al., "Glycated Hemoglobin," Current Science, vol. 83, No. 12, pp. 1522-1532 (Dec. 2002).

Nathan et al., "Relationship between Glycated Haemoglobin Levels and Mean Glucose Levels over Time," Diabetologia, No. 50, pp. 2239-2244 (2007).

Rohlfing et al., "Defining the Relationship between Plasma Glucose and HbA1c," Diabetes Care, vol. 25, No. 2, pp. 275-278 (Feb. 2002).

Mathworld—A Wolfram Web Resources, "Exponential_Decay" , p. 1 retrieved from http://mathworld.wolfram.com/ExponentialDecay.html (last updated Aug. 7, 2012).

Tahara et al., "Kinetics of HbA1c, Glycated Albumin, and Fructosamine and Analysis of Their Weight Functions Against Preceding Plasma Glucose Level," Diabetes Care, vol. 18, No. 4, pp. 440-447 (Apr. 1995).

Tahara et al., "The Response of GHb to Stepwise Plasma Glucose Change Over Time in Diabetic Patients," Diabetes Care, vol. 16, No. 9, pp. 1313-1314 (Sep. 1993).

Nuttall et al., "Metabolic Response of People with Type 2 Diabetes to a High Protein Diet," Nutrition & Metabolism, No. 1:6, pp. 1-7 (2004).

Ramlo-Halsted et al., "The Natural History of Type 2 Diabetes: Practical Points to Consider in Developing Prevention and Treatment Strategies," Clinical Diabetes, vol. 18, No. 2, pp. 1-10 (2000).

(56) References Cited

OTHER PUBLICATIONS

Simpson et al., "Macronutrients Have Different Metabolic Effects in Nondiabetics and Diabetics," The American Journal of Clinical Nutrition, No. 42, pp. 449-453 (Sep. 1985).
Gannon et al., "Oral Arginine Does Not Stimulate an Increase in Insulin Concentration but Delays Glucose Disposal," The American Journal of Clinical Nutrition, No. 76, pp. 1016-1022 (2002).
Mander et al., "Co-Ingestion of a Protein Hydrolysate and Amino Acid Mixture with Carbohydrate Improves Plasma Glucose Disposal in Patients with Type 2 Diabetes," the American Journal of Clinical Nutrition, No. 82, pp. 76-83 (2005).
Van Loon et al., "Amino Acid Ingestion Strongly Enhances Insulin Secretion in Patients with Long-Term Type 2 Diabetes," Diabetes Care, vol. 26, No. 3, pp. 625-630 (Mar. 2003).
Golkar, S. M. et al., "Assessment of the relationship between glucose and A1c using kinetic modeling", Journal of Diabetes and Its Complications 20 (2006) 285-294.
Kovatchev, B. P. et al., "Algorithmic Evaluation of Metabolic Control and Risk of Severe Hypoglycemia in Type 1 and Type 2 Diabetes Using Self-Monitoring Blood Glucose Data", diabetes Technology and Therapeutics, vol. 5, No. 5, 2003, p. 817-828.
Svendsen, P. A. et al., "Glycosylated Haemoglobin and Steady-State Mean Blood Glucose Concentration in Type 1 (insulin-Dependent) Diabetes", Diabetologia (1982) 23:403-405.
Chan et al., "Pharmacological Management of Type 2 Diabetes Mellitus: Rationale for Rational Use of Insulin," Mayo Clinic Proc., No. 78, pp. 459-467 (2003).
Shafiqul et al., "Peak Blood Glucose Prediction Algorithm Following a Meal Intake," IEEE Canadian Conference on Electrical and Computer Engineering, pp. 579-582 (Jul. 30, 2007).
Tresp et al., "Neural Network Models for the Blood Glucose Metabolism of a Diabetic," IEEE Transactions of Neural Networks, pp. 1-24 (1999).
Reed, K. et al. "Interactive Educational Diabetes/Insulin Tutorial at www.2aida.info", Diabetes Technology & Therapeutics, vol. 8, No. 1, p. 126-137 (2006).
Bergman, et al., "Quantitative Estimation of Insulin Sensitivity," The American Physiological Society, No. 236(6), p. E667-E677 (1979).
"Insulin Activity Curves," pp. 1-2, retrieved from http://members.tripod.com/diabetics_world/Human_Animal_Activity.htm#Human (last visited Aug. 10, 2012).
Eli Lilly Co., Ltd., "Insulin Humaject Information" retrieved from http://www.drugs.com/uk/humaject-pens-prefilled-insulin-pens-soluble-mixture-3-spc-3458.html (last visited Aug. 2011).
"Chapter Two Rate of Change: The Derivative," pp. 1-44, retrieved from http://media.wiley.com/product_data/excerpt/63/EHEP0005/EHEP000563-2.pdf (last visited Aug. 10, 2012).
Lilly USA, LLC., "Highlights of Prescribing Information," May 18, 2011 pp. 1-12.
Stickle D. et al. "A kinetic mass balance model for 1, 5-anhydroglucitol: applications to monitoring of glycemic control", Endocrynology and Metabolism, vol. 273, No. 4, p. E821, Jan. 1, 1997.
McGill J. B. et al. "Circulating 1, 5-anhydroglucitol levels in adult patients with diabetes reflect longitudinal changes of glycemia: a U.S. trial of the GlycoMark assay", Diabetes Care, american Diabetes Association, alexandria, VA, US, vol. 27, No. 8, p. 1859-1865, Aug. 1, 2004.
Nowatzke W. et al. "Evaluation of an assay for serum 1, 5-anhydroglucitol(GlycoMark™) and determination of reference intervals on the Hitachi 917 analyzer", Clinical Chimica ACTA, Elsevier BV, Amsterdam, NL, vol. 350, No. 1-2, p. 201-209, Dec. 1, 2004.
Albisser et al., "Home Blood Glucose Prediction: Validation, Safety, and Efficacy Testing in Clinical Diabetes," Diabetes Technology Therapeutics, Jun. 2005, vol. 7, No. 3, pp. 487-496.
Albisser et al., "Home Blood Glucose Prediction: Clinical Feasibility and Validation in Islet Cell Transplantation Candidates," Diabetologia, Jul. 2005, vol. 48, No. 7, pp. 1273-1279.
Rohlfing et al., "Defining the Relationship Between Plasma Glucose and HbA(1c): Analysis of Glucose Profiles and HbA(1c) in the Diabetes Control and Complications Trial," Diabetes Care, Feb. 2002, vol. 25, No. 2, pp. 275-278.
Albisser and Inhaber, "Automation of the Consensus Guidelines in Diabetes Care: Potential Impact on Clinical Inertia," Endocrine Practice, Nov.-Dec. 2010, vol. 16, No. 6, pp. 992-1002.
Albisser et al., "Closing the Circle of Care with New Firmware for Diabetes: MyDiaBase+RxChecker," J Diabetes Sci Technol., May 2009, vol. 3, No. 3, pp. 619-623.
Albisser et al., "Prescription Checking Device Promises to Resolve Intractable Hypoglycemia," J Diabetes Sci Technol., May 2009, vol. 3, No. 3, pp. 524-532.
Albisser, "Technophobia, Prescription Checking and the Future of Diabetes Management," Diabetologia, Jun. 2009, vol. 52, No. 6, pp. 1013-1018.
Choleau et al., "A Novel Method for Assessing Insulin Dose Adjustments by Patients with Diabetes," J Diabetes Sci Technol., Jan. 2007, vol. 1, No. 1, pp. 3-7.
Albisser et al., "Averting Iatrogenic Hypoglycemia Through Glucose Prediction in Clinical Practice: Progress towards a New Procedure in Diabetes," Diabetes Res Clin Pract., May 2007, vol. 76, No. 2, pp. 207-214.
Albisser et al., "How Good is Your Glucose Control?" Diabetes Technol Ther., Dec. 2005, vol. 7, No. 6, pp. 863-875.
Albisser, "A Graphical User Interface for Diabetes Management That Integrates Glucose Prediction and Decision Support," Diabetes Technol Ther., Apr. 2005, vol. 7, No. 2, pp. 264-273.
Albisser et al., "Patient Confidentiality, Data Security, and Provider Liabilities in Diabetes Management," Diabetes Technol Ther., 2003, vol. 5, No. 4, pp. 631-640.
Albisser, "Analysis: Toward Algorithms in Diabetes Self-Management," Diabetes Technol Ther., 2003, vol. 5, No. 3, pp. 371-373.
Albisser A.M. et al., "The Impact of Initiatives in Education, Self-Management Training, and Computer-Assisted Self-Care on Outcomes in Diabetes Disease Management," Diabetes Technol Ther., 2001 Winter, vol. 3, No. 4, pp. 571-579.
Albisser et al., "Information Technology and Home Glucose Clamping," Diabetes Technol Ther., 2001 Fall, vol. 3, No. 3, pp. 377-386.
Albisser, "Clinical Studies with Home Glucose Clamping," Ann Endocrinol (Paris), Feb. 2001, vol. 62 No. 1, Pt 1, pp. 11-18.
Albisser et al., "Getting Referrals for Diabetes Education and Self-Management Training," Diabetes Educ., Nov.-Dec. 1999, vol. 25 No. 6, pp. 959-960, 963-964, 966 passim.
Meneghini, et al., "An Electronic Case Manager for Diabetes Control," Diabetes Care., Apr. 1998, vol. 21, No. 4, pp. 591-596.
Naylor et al., "Comparison of Parametrized Models for Computer-Based Estimation of Diabetic Patient Glucose Response," Med Inform (Lond), Jan.-Mar. 1997, vol. 22, No. 1, pp. 21-34.
Albisser et al., "Diabetes Intervention in the Information Age," Med Inform (Lond), Oct.-Dec. 1996, vol. 21, No. 4, pp. 297-316. Erratum in: Med Inf (Lond), Apr.-Jun. 1997, vol. 22, No. 2, p. 205.
Angelico et al., "Use of an On-Line Computer System for Quantifying Insulin Requirements Before and After Islet Cell Transplantation: First Experience," Transplant Proc., Dec. 1995, vol. 27, No. 6, p. 3173.
Rodbard et al., "American Association of Clinical Endocrinologists Medical Guidelines for Clinical Practice for the Management of Diabetes Mellitus," Endocr Pract., May-Jun. 2007, vol. 13, Suppl. 1, pp. 1-68.
Rodbard et al., "Statement by an American Association of Clinical Endocrinologists/American College of Endocrinology Consensus Panel on Type 2 Diabetes Mellitus: an Algorithm for Glycemic Control," Endocr Pract., 2009, vol. 15, No. 6, pp. 540-559.
Funnell et al., "National Standards for Diabetes Self-Management Education," Diabetes Educ. 2007, vol. 33, No. 4, pp. 599-614.
Lachin et al., "Effect of Glycemic Exposure on the Risk of Microvascular Complications in the Diabetes Control and Complications Trial—Revisited," Diabetes. Apr. 2008, vol. 57, No. 4, pp. 995-1001.
Nathan, "Finding new treatments for diabetes—how Many, How Fast, . . . How Good?" N Engl J Med, Feb. 2007, vol. 356, No. 5, pp. 437-440.

(56) References Cited

OTHER PUBLICATIONS

Diabetes Control and Complications Trial Research Group, "The Effect of Intensive Treatment of Diabetes on the Development and Progression of Long-Term Complications in Insulin-Dependent Diabetes Mellitus," N Engl J Med, Sep. 1993, vol. 329, No. 14, pp. 977-986.

Hirsch et al., "A Real-World Approach to Insulin Therapy in Primary Care Practice," Clinical Diabetes, 2005, vol. 23, No. 2, pp. 78-86.

UK Prospective Diabetes Study Group, "Intensive Blood-Glucose Control with Sulphonylureas or Insulin Compared with Conventional Treatment and Risk of Complications in Patients with Type 2 Diabetes (UKPDS 33)," Lancet, Sep. 1998, vol. 352, Issue 9131, pp. 837-853.

The DCCT Research Group, "Epidemiology of severe hypoglycemia in the Diabetes Control and Complications Trial," Am J Med., Apr. 1991, vol. 90, pp. 450-459.

Cryer, "Hypoglycemia: Still the Limiting Factor in the Glycemic Management of Diabetes," Endocr Pract., Sep. 2008, vol. 14, No. 6, pp. 750-756.

Laprie (Ed), "Dependability: Basic Concepts and Terminology," Springer-Verlag, Wein, New York, 1992.

Drab, "Translating Clinical Guidelines into Clinical Practice: Role of the Pharmacist in Type 2 Diabetes Management," J Am Pharm Assoc., Nov.-Dec. 2009, vol. 49, No. 6, pp. 152-162.

Kirwin et al., "Pharmacist Recommendations to Improve the Quality of Diabetes Care: A Randomized Controlled Trial," Journal of Managed Care Pharmacy, Mar. 2010, vol. 16, No. 2, pp. 104-113.

Armor et al., "A Review of Pharmacist Contributions to Diabetes Care in the United States," Journal of Pharmacy Practice, 2010, vol. 23, No. 3, pp. 250-264.

Campbel, "Role of the Pharmacist in Diabetes Management," Am J Health-Syst Pharm, Dec. 2002, vol. 59, Suppl. 9, pp. S18-S21.

Palaian et al., "Role of Pharmacist in Counseling Diabetes Patients," The Internet Journal of Pharmacology, 2005, vol. 4, No. 1.

Worthington, "Controlling Boold Glucose: Insights from an Engineering Control Systems Perspective," Med Inform, 1997, vol. 22, No. 1, pp. 5-19.

Canadian Pharmacists Association, "The Diabetes Strategy for Pharmacists," http://diabetespharmacists.ca/ (last visited Aug. 10, 2012).

Life Scan, Inc., "One Touch Verio IQ Blood Glucose Monitoring System Owner's Booklet: Instructions for Use," Mar. 2011.

Deutsch T. et al., "The principles and prototyping of a knowledge-based diabetes management system", Computer methods and programs in biomedicine, Elsevier, Amsterdam, NL vol. 29, No. 2, Jun. 1, 1989, pp. 75-88.

* cited by examiner

Figure 4

| Medical Center: | Central Hospital | | | | | | | | | | Circadian Profiles ← 61 | | |
|---|---|---|---|---|---|---|---|---|---|---|---|---|---|
| Physician: | R. Kimble, MD | | | | | | | | | | MPP Start Date: Sep 5, 2011 | | |
| Patient: | Dan Cooper | | | Hx Number: 487 52 9733 | | | | | | | Height: 74 | | |

| MP Profiles | Breakfast {63} | | | Lunch {64} | | | Dinner {65} | | | Bedtime {66} | | |
|---|---|---|---|---|---|---|---|---|---|---|---|---|
| | Before B | After B | Mid B-L | Before L | After L | Mid L-D | Before D | After D | Mid D-S | Before S | After S | Over Night |
| BW1: 209 | | | | | | | | | | | | |
| SMBG (hh:mm) | 194 7:10 | 63 8:40 | | 144 13:50 | 163 15:20 | | 141 17:20 | 48 18:50 | | 123 22:00 | | 124 3:30 |
| Medications Shorter-acting | 6 Apidra | | Site T | 4 Apidra | | Site T | 6 Apidra | | Site T | | | Site T |
| Longer-acting | | | | | | | | | | 18 Lantus | | |
| Life-style comments (Optional) | CHO EX Stress etc | | | CHO EX Stress etc | | | CHO EX Stress etc | | | CHO EX Stress etc | | |

| MP Profiles | Breakfast {63} | | | Lunch {64} | | | Dinner {65} | | | Bedtime {66} | | |
|---|---|---|---|---|---|---|---|---|---|---|---|---|
| | Before B | After B | Mid B-L | Before L | After L | Mid L-D | Before D | After D | Mid D-S | Before S | After S | Over Night |
| BW2: 206 | | | | | | | | | | | | |
| SMBG (hh:mm) | 167 8:50 | 99 10:20 | | 99 14:00 | 211 15:30 | | 122 18:30 | 60 20:00 | | 120 21:50 | | 180 2:50 |
| Medications Shorter-acting | 6 Apidra | | Site T | 4 Apidra | | Site T | 6 Apidra | | Site T | | | Site T |
| Longer-acting | | | | | | | | | | 18 Lantus | | |
| Life-style comments (Optional) | CHO EX Stress etc | | | CHO EX Stress etc | | | CHO EX Stress etc | | | CHO EX Stress etc | | |

Circadian Profiles — Central Hospital

| Medical Center: | Central Hospital | | | | | | | | | | |
|---|---|---|---|---|---|---|---|---|---|---|---|
| Physician: | R. Kimble, MD | | | | | MPP Start Date: Sep 5, 2011 | | | | | |
| Patient: | Dan Cooper | | Hx Number: 487 52 9733 | | | | | | Height: 74 | | |

| MP Profiles | Breakfast | | | Lunch | | | Dinner | | | Bedtime | |
|---|---|---|---|---|---|---|---|---|---|---|---|
| BW1: 209 | Before B | After B | Mid B-L | Before L | After L | Mid L-D | Before D | After D | Mid D-S | Before S | After S | Over Night |
| SMBG (hh:mm) | 100 7:15 | 120 8:30 | | 100 12:30 | 120 13:15 | | 100 17:00 | 120 18:00 | | 100 22:00 | | 130 3:30 |
| Medications Shorter-acting | 6 Apidra | Site T | | 4 Apidra | Site T ◆ | | 6 Apidra | Site T | | | Site T | |
| Longer-acting | | | | | | | | | | 18 Lantus | | |
| Life-style comments (Optional) | Usual after lunch activity increased with mild exercise at level 1. { 151 | | | | | | | | | | |

{ 142

| MP Profiles | Breakfast | | | Lunch | | | Dinner | | | Bedtime | |
|---|---|---|---|---|---|---|---|---|---|---|---|
| BW2: 206 | Before B | After B | Mid B-L | Before L | After L | Mid L-D | Before D | After D | Mid D-S | Before S | After S | Over Night |
| SMBG (hh:mm) | 167 8:50 | 99 10:20 | | 99 14:00 | 211 15:30 | | 122 18:30 | 60 20:00 | | 120 21:50 | | 180 2:50 |
| Medications Shorter-acting | 6 Apidra | Site T | | 4 Apidra | Site T | | 6 Apidra | Site T | | | Site T | |
| Longer-acting | | | | | | | | | | 18 Lantus | | |
| Life-style comments (Optional) | CHO EX Stress etc | | | CHO EX Stress etc | | | CHO EX Stress etc | | | CHO EX Stress etc | | |

150

COMPUTER-IMPLEMENTED SYSTEM AND METHOD FOR IMPROVING GLUCOSE MANAGEMENT THROUGH CLOUD-BASED MODELING OF CIRCADIAN PROFILES

FIELD

The present invention relates in general to glycemic management in diabetic patients and, in particular, to a computer-implemented system and method for improving glucose management through cloud-based modeling of circadian profiles.

BACKGROUND

As a chronic and incurable disease, diabetes mellitus requires continuing care that lasts throughout the life of the patient. Both caregivers and patients alike are primarily expected to play an active role in managing diabetes, regardless of form, whether Type 1, Type 2, gestational, or other. Secondarily, family, friends and peers in the diabetic disease state play an important behind-the-scenes supporting role in ongoing glucose management. Diabetes patients are typically coached by their caregivers on lifestyle modification and educated to understand the affects of diet, especially carbohydrates, body weight, physical activity, medications, and stress on their diabetic condition. Diabetes patients are also trained and encouraged to regularly test and record their blood glucose levels. In addition, medication-treated patients learn to undertake daily self-administration of medications and, where appropriate, determine corrective medication dosing to counteract postprandial glycemic rise. All diabetes patients are expected to document their self-care in a daily diary that typically chronicles self-monitored blood glucose values, medications, physical activity, and dietary intake.

In turn, caregivers follow their diabetes patients on a periodic basis and work to ensure their compliance with the consensus guidelines and mandatory targets (CG&MT), which have been formulated and are regularly updated by the American Association of Clinical Endocrinologists (AACE) and the American College of Endocrinology (ACE), as well as the American Diabetes Association (ADA). At each patient consultation, a caregiver may evaluate the patient's daily diary to identify patterns in the pre-meal data, which can include examining particular examples of the patient's actions to determine underlying causes for any outcomes suffered, above all, episodes of hypoglycemia. Additionally, the caregiver will normally test the patient's level of glycated hemoglobin ("A1c") to establish accord with the current CG&MT target for well-managed diabetes. As needed, the caregiver may adjust the patient's oral anti-diabetic medications or insulin dosing to hopefully move the patient's blood glucose and A1c levels closer to the mandated targets.

The roles respectively performed by caregivers and their diabetic patients form a "circle of care" that requires each patient to provide their own data and do those actions necessary that together allow the caregivers to effectively manage the patient's diabetic condition. At a minimum, each patient is expected to self monitor their blood glucose levels and comply with each caregiver's instructions. Obversely, the caregivers are expected to monitor the patient's condition and provide apt guidance through changes in medications and lifestyle as needed to achieve perfect diabetes control as mandated in the various guidelines.

Notwithstanding, the circle of care generally remains incomplete. Conventional diabetes management efforts are in practice remarkably retrospective due to the significant focus on past patient condition, as seen through the patient's self-monitored blood glucose values that ordinarily extend back over several prior months. In turn, armed at best with the historical values of blood glucose testing, as sometimes confirmed by A1c results, a caregiver endeavors to control the future direction of ongoing diabetes treatment typically for the next several months until the next consultation. This control is exercised chiefly by making adjustments to medications, typically focused on insulin, with the intent of somehow moving patient blood glucose levels and A1c to target, and often without demanding data more reflective of the patient's true condition at the time of consultation.

In practice, the circle of care also suffers from imbalance. From a caregiver perspective, the circle of care is generally viewed as a closed two-way exchange between the caregiver and the patient, even though the caregiver often refers the patient to outside diabetes educational and support resources. Conversely, from a patient perspective, the circle of care simply begins with the caregiver and continues with the support community that helps the patient cope with and manage the disease. Although the contribution of a support community to a patient's well being is merely intrinsic and is not strongly factored into the caregiver's immediate treatment approach, such support nevertheless is invaluable and provides the patient with a venue for sharing experiences and imparts understanding, motivation and hope in spite of the chronic nature of diabetes.

The incompleteness of the circle of care also contributes to the dilemma faced by caregivers in managing diabetes, which suggests that satisfactory glycemic control is seemingly only achievable with unsatisfactory risk of hypoglycemia, as well as the converse. The CG&MT recommends a fasting blood glucose level of less than 110 mg/dL (non-fasting less than 140 mg/dL) and A1c between 6% and 7%, with patients generally being asked to strive for A1c of less than 7% (and less than 6.5% according to other standards). Achieving these goals, however, carries the adverse consequence of increasing the risks of treatment-related hypoglycemia, which caregivers counter by changing diet or medication dosing that then shifts that patient's blood glucose level outside the CG&MT target range. Consequently, a self-reinforcing vicious cycle is formed, as increased medication dosing to reduce glycemic values into mandated target ranges results in increased hypoglycemic risk that a patient must counteract by eating more with an ensuing gain in body weight that induces further diabetes medication dosing change.

Therefore, a need remains for providing an improved approach to glycemic control that shifts the focus of diabetes management efforts away from retrospective blood glucose histories to recent and representative glycemic indications that better tie caregiver efforts and glucose management to actual, realized and timely patient need, and which opens up the circle of care to the support community that helps patients in dealing with diabetes day-to-day.

SUMMARY

A predictive circadian profile that accurately models expected blood glucose values and their expected error can be created by using only the SMBG data stored in a near-term observational time frame, typically a week, immediately preceding the next caregiver consultation. Only validated (recent and typical) SMBG values are used in predicting expected glycemic outlook, thereby ensuring a reliable model. The circadian profile can be shared online with the patient's support community, with the assistance of social networking media and the so-called "cloud" computing infrastructure, and their feedback can be factored into ongoing glucose management efforts. During patient consultations, the caregiver can explore changes to medication dosing, which can include all manner of anti-diabetes drugs, including insulin and oral agents, with confidence that the new dosing will both move the patient's glycemic control into the desired target ranges and avoid the deleterious risk of treatment-related hypoglycemia.

One embodiment provides a computer-implemented system and method for improving glucose management through cloud-based modeling of circadian profiles. For each of a plurality of daily meal periods occurring over a recent observational time frame, at least two sets of pre- and post-meal period data that include a blood glucose level and a diabetes medication dosing are stored online into a circadian profile for a diabetic patient in a cloud computing infrastructure. Predicted blood glucose for the patient is modeled over the cloud computing infrastructure. Access to the circadian profile is validated. A model, including expected blood glucose values and their predicted errors at each daily meal period is created from the blood glucose levels in each record in the validated circadian profile. The model of the expected blood glucose values and their predicted errors is visualized in a preferably log-normal distribution. Target ranges for blood glucose are determined at each meal period and the target ranges are superimposed over the expected blood glucose values. Pharmacodynamics of the diabetes medication are obtained. An incremental change in dosing of the identified diabetes medication is propagated over the model day and the expected blood glucose values and their predicted errors are adjusted in response to the suggested incremental dosing change.

A further embodiment provides a computer-implemented system and method for managing diabetes through cloud computing with circadian profiles. A database, including a plurality of records, is structured. Each record includes a circadian profile. Each circadian profile is divided into meal period categories. Typical measurements of pre-meal and post-meal self-measured blood glucose occurring over a recent observational time frame are stored into each of the meal period categories in at least two of the circadian profiles. Diabetes medication dosed during each of the meal period categories is identified in at least two of the circadian profiles. The database is maintained in a cloud computing infrastructure. Predicted blood glucose levels are modeled. Access through the cloud computing environment is restricted to validated users. Upon validation, the self-measured blood glucose measurements are collected along a category axis comprising each of the meal period categories. Expected blood glucose values and their predicted errors are determined from the self-measured blood glucose measurements at each meal period category on the category axis and the expected blood glucose values and their predicted errors for a model day are visualized in a log-normal distribution. A suggested incremental change in dosing of the diabetes medication is propagated over the model day and the visualized expected blood glucose values and their predicted errors are adjusted based on pharmacodynamics of the diabetes medication in proportion to the incremental change in dosing.

For certain types of diabetes patients, the approach removes the need for repeated SMBG testing throughout each day and extending over the entire course of time separating caregiver consultations. Type 2 diabetes patients, for instance, would only need to collect a minimum of two SMBG results per meal period in the week prior to consultation. Moreover, with this approach, glycemic management can be performed in an intermittent "batch" processing fashion and not in real time.

The approach also enhances caregiver confidence, as the predicted blood glucose levels and their error ranges are based on recent and typical patient data. The caregiver is then able to treat to target and safely prescribe medication dosing changes, which can include all manner of anti-diabetes drugs, including insulin and oral agents, with a high degree of confidence of attaining the results desired.

Finally, the approach broadens the span of the circle of care by including the patient's support community as an integral part of glucose management efforts. Peers in the disease state can share in their experiences online and provide inputs that can compliment and reinforce formal caregiver guidance. Peers can also share and compare their circadian profiles; earn rewards, such as badges, stars or status in the online community for reaching milestones; and compete with peers for perfect diabetes control.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIG. 4 is a user interface diagram showing, by way of example, an interactive screen for a circadian profile for use in the system of FIG. 1.

FIG. 12 is a user interface diagram showing, by way of example, an interactive screen for a circadian profile for use in a further embodiment of the system of FIG. 1.

DETAILED DESCRIPTION

Figure 1:
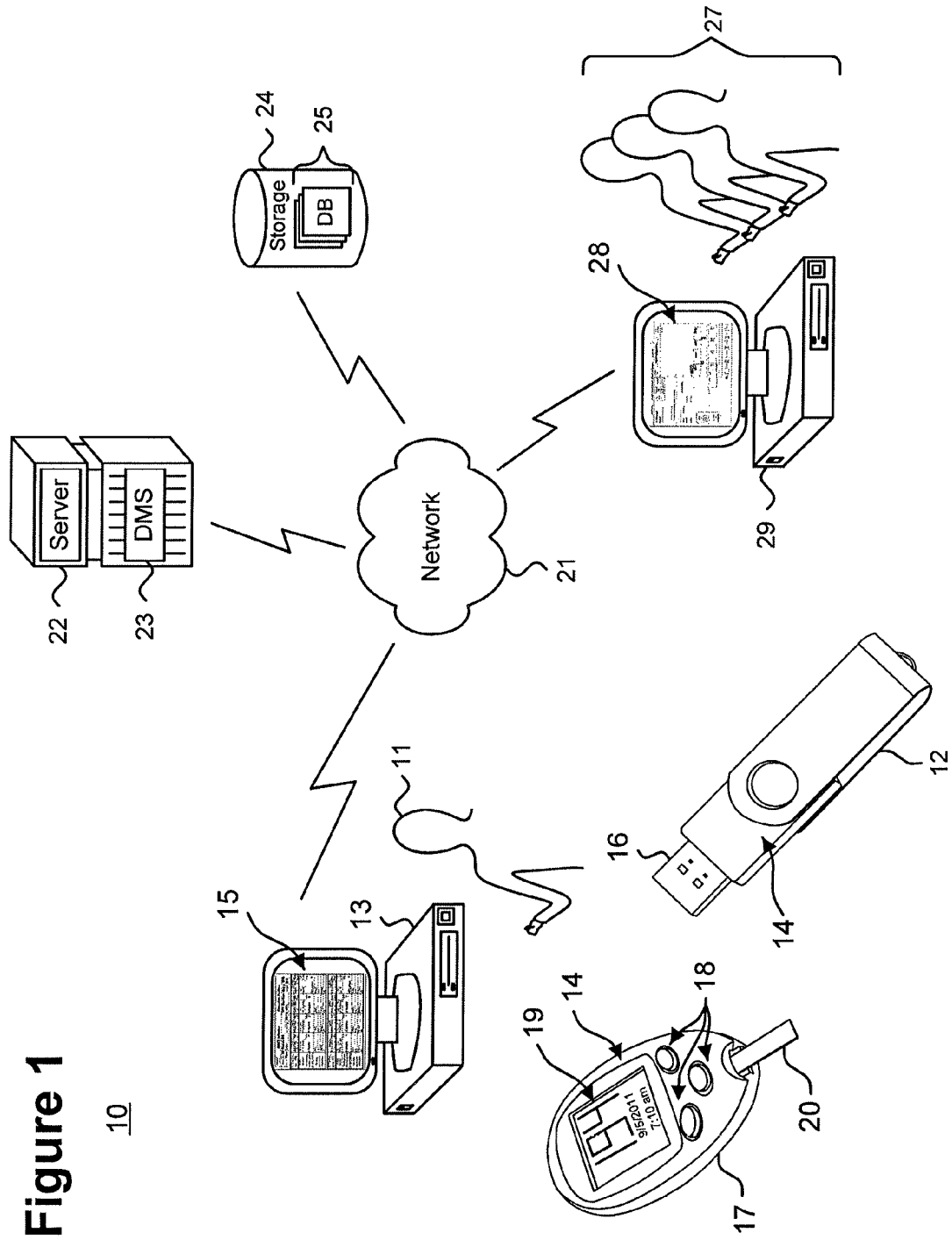
FIG. 1 is a block diagram showing a computer-implemented system for improving glucose management through cloud-based modeling of circadian profiles, in accordance with one embodiment.

Ideal glycemic control in a diabetes patient occurs when the average value of self-measured blood glucose (SMBG) at each point in a circadian diabetes profile falls within a specific target range. The efficacy of current diabetes control can be improved to help make possible ideal glycemic management by harnessing the statistical properties of blood glucose and biologic rhythmicity, when represented as categorical, not time series, data, to predict circadian profiles of expected blood glucose values. FIG. 1 is a block diagram showing a computer-implemented system 10 for improving glucose management through cloud-based modeling of circadian profiles, in accordance with one embodiment. Circadian profiles close the heretofore-incomplete circle of care and remove the danger of clinical diabetes medication prescription errors, which have been caused by overly retrospective glycemic focus and chiefly by making adjustments to medications, typically focused on insulin.

The system 10 is loosely grouped into three sets of components. First, a patient-oriented structured database 14 stores SMBG values, medication dosing for all types of anti-diabetes drugs, including insulin and oral agents, and related information for a diabetes patient 11 on a portable media device 12, such as a USB flash drive or other form of non-transitory removable computer-readable storage medium, such as described in commonly-assigned U.S. Patent application Publication No. 2014/0032196, pending, the disclosure of which is incorporated by reference. The SMBG measurements are typically obtained from a conventional glucose meter ("glucometer"). Once a complete circadian profile has been created, as further described infra with respect to FIG. 2, the database 14 is uploaded from a personal or laptop computer 13 or mobile computing device (not shown), such as a smart phone, onto a wide area public data network 21, such as the Internet, or other network infrastructure. A caregiver-centric consultation program 15 executes on a personal or laptop computer 13 or mobile computing device and enables a diabetes patient 11 to access the database 14 as stored on the portable media device 12. To upload the database 14, the portable media device 12 is interfaced via a built-in data interface port 16, such as a USB interface plug or other wireless or wired adapter, with the personal or laptop computer 13, mobile computing device, or other compatible computing device, which then loads the necessary program, library and data files from the portable media device 12.

In a further embodiment, the database 14 could be integrated into a glucometer 17 or other type of portable blood glucose testing device with onboard data collection capabilities, such as described in commonly-assigned U.S. Patent application Publication No. 2014/0032195, pending, the disclosure of which is incorporated by reference. The glucometer 17 is a "smart" suitably-programmed glucometer that includes an internal memory that electronically records the results of each blood glucose test, along with the date and time of testing, into the database 14. Additionally, the glucometer 17 has a visual display 19 and a set of input controls 18 that together form a user interface through which SMBG testing and diabetes medication dosing data, as well as other optional but useful patient information, can be entered. When in use by the patient 11, the glucometer 17 calculates and displays blood glucose levels by reading a disposable test strip 20 upon which the patient 11 has placed a drop of blood. With the reading of the test strip 20, the patient 11 uses the input controls 18 to validate and then identify the current category of meal period and the SMBG measurement is then stored by the glucometer 17 into the patient's circadian profile under the indicated meal period category. The patient's diabetes management data is later offloaded to a suitably-programmed computer, such as the personal or laptop computer 13 or mobile computing device via a built-in data interface port, such as a USB interface plug or other wireless or wired adapter, which is then uploaded onto the network 21. In a further embodiment, the glucometer 17 is provided as an external "glucophone," that is, a smart phone that has a built-in or add-on glucometer, and the database 14 and the program 15 are stored on and maintained by the glucophone. Still other types of devices for storing diabetes management data into the database 14 are possible, for instance, a tablet or network computer. In addition, other intermediary devices for uploading the diabetes management data onto the network 21 are possible, such as a Web-enabled smart phone that has a built-in or add-on glucometer for measuring SMBG levels and is able to upload data directly onto the network 21.

Second, each patient's diabetes management data is stored and evaluated online. This online storage and evaluation of patient data utilizes the flexibility and ubiquity of a so-called "cloud" computing infrastructure that dissociates the need for supplying dedicated computing resources to each patient and caregiver and instead entrusts the provisioning of data storage and computation to a distributed network-based service paradigm. The patient's data are externally stored in an online database 25, which is secured, private and password-protected, and both current and previously stored data can be accessed. In one embodiment, the diabetes management data is stored in an online database 25, which is maintained in storage 24 that is interfaced over the network 21, although the database 25 could also be stored using several different storage arrangements that could each be tied to a single physical data server or to different servers under a common data access front-end. Still other online structurings of the storage of the database 25 are possible.

Figure 5:
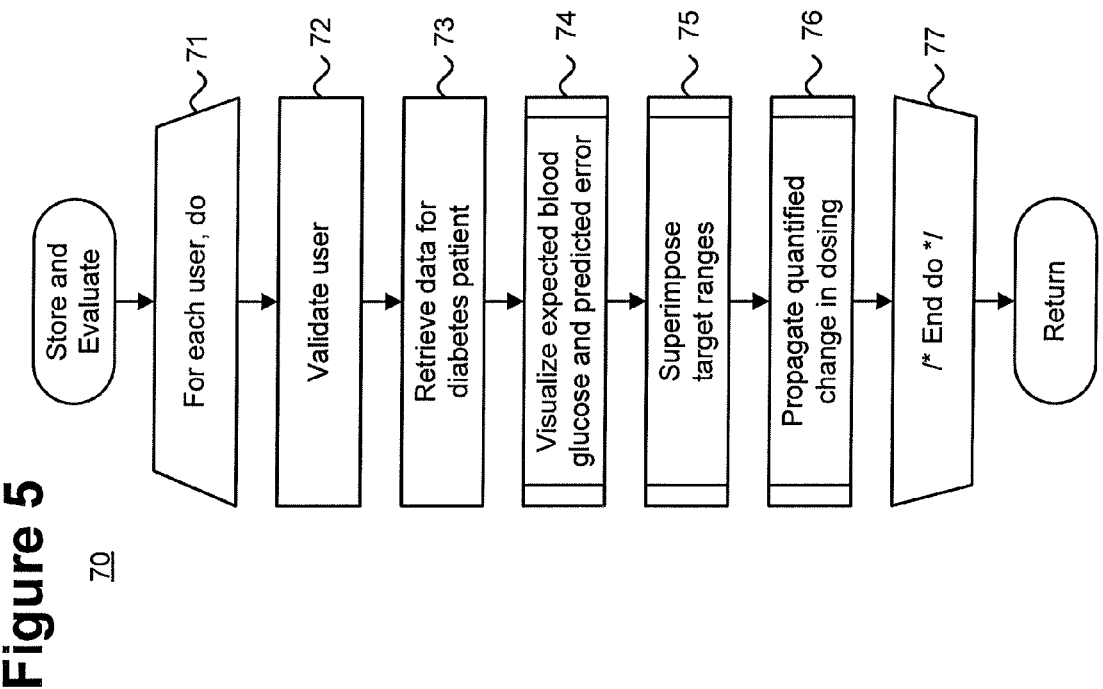
FIG. 5 is a flow diagram showing a routine for storing and evaluating uploaded meal period data for use in the method of FIG. 2.

Finally, a server 22 executes a diabetes management server 23 (DMS) through which online users 27, including the caregiver and patient 11, as well as the patient's support community, are able to collaboratively access, evaluate and share the diabetes management data in the database 25 online, as further described infra with reference to FIG. 5. Through the DMS 23, the users 27 can execute a caregiver-centric consultation program 28 on a personal or laptop computer 29, mobile computing device, or other network-capable device, including a Web-enabled smart phone. The DMS 23 validates each user 27 to ensure legitimate access and retrieves patient diabetes data from the database 25 in response to the program 28, which can then generate predictive circadian profiles for use in following diabetes patients and ensuring their CG&MT compliance, but without the dilemma of treatment-induced increased hypoglycemic risk. Upon initial execution, the database 25 and program 28 are personalized with the patient's and his caregiver's demographic information, as appropriate, after which the patient can add additional SMBG values, lifestyle, and diabetes medication details for all types of anti-diabetes drugs, including insulin and oral agents. His caregiver performs a similar installation process and executes the program 28, which provides circadian profile-based predictions of blood glucose values and their expected errors, incremental suggestions and modeling of changes to medication dosing, and diabetes patient counseling points.

Figure 2:
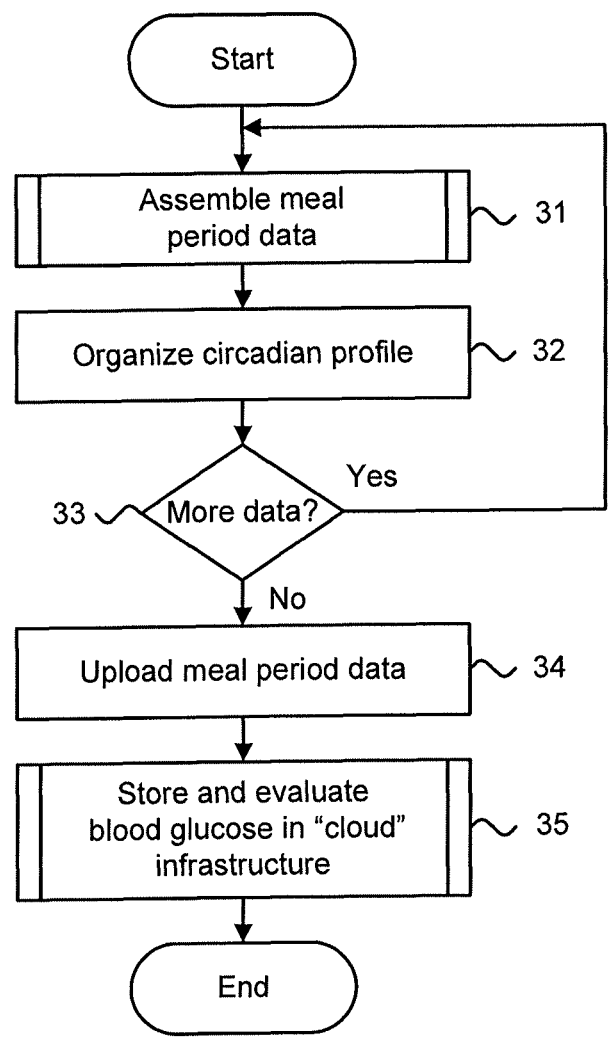
FIG. 2 is a flow diagram showing a computer-implemented method for improving glucose management through cloud-based modeling of circadian profiles, in accordance with one embodiment.

The database 14 and program 15 collaboratively facilitate the achievement of improving glycemic management by respectively chronicling relevant patient self-management efforts and predictively modeling glycemic outcomes for caregiver review and utilization. FIG. 2 is a flow diagram showing a computer-implemented method 30 for improving glucose management through cloud-based modeling of circadian profiles, in accordance with one embodiment. The method 30 can be implemented in software, such as through the databases 14, and programs 15, 28, and execution of the software can be performed on a computer system 10, such as described supra with reference to FIG. 1, as a series of process or method modules or steps.

By way of overview, a patient's SMBG measurements and accompanying dosing of diabetes medications, including insulin and oral agents, are entered into a circadian profile that is stored in the structured database 14. The circadian profile is implemented using a format that affords a one-to-one correspondence with the CG&MT mandated target ranges of blood glucose values and is organized as data records in the database 14. The circadian profile structures daily SMBG measurements and medication dosing into a data series of pre-meal and timed post-meal categories. A day is modeled as a complete data series, even though the actual patient data within a particular "day" may actually have been collected on different calendar days falling within the observational time frame. In one embodiment, each modeled day is divided into meal periods for breakfast, lunch and dinner, and one additional "meal" period from pre-bedtime through overnight to pre-breakfast, which is actually a period of fasting. Each data series includes one pre-meal SMBG value and diabetes medication dosing for each of breakfast, lunch, and dinner (three SMBG values) and one timed post-meal period SMBG value also for each of breakfast, and dinner (three more SMBG values), plus one timed post-meal period SMBG value both pre-bedtime and overnight. In addition, notations on daily lifestyle chronicling physical activity, diet and stress at each meal period, and daily body weight can be included in the data record. Still other patient- and treatment-related data can also be stored in the database 14.

The program 15 implements a statistical engine that regards the blood glucose values as categories and not as a time series, that is, temporal events based on actual "clock" time. A time series creates a time vector problem. For example, consider the averaging of continuous diurnal glucose readings for a patient's breakfast. On one day, say, Saturday, breakfast may occur at 6:30 am, while the next day, the patient decides to sleep in and breakfast may consequently occur at 8:15 am. The later occurrence of Sunday's breakfast at 8:15 am causes that diurnal glucose reading to temporally coincide with the peak post-meal diurnal glucose reading of Saturday, which causes the averaging of the wrong blood glucose values. To avoid the time vector problem, the blood glucose data is transformed from a time series axis to a category axis, where the correct pre- and timed post-meal blood glucose values are collected according to their descriptive labels, not clock time. The use of categories enables the blood glucose value to be both predictable and modelable using a log-normal statistical distribution for a model day.

A further advantage of using a category axis is being able to automatically synchronize bolus and basal doses to both span the time period beginning at just before a meal period all the way through to just before the next meal period. Conventional insulin pump manufacturers often program basal rates according to clock times that may not necessarily correspond to pre-meal times. Diabetes patients 11 who use an insulin pump are typically given the freedom to change their meal times or even skip meals altogether. Consequently, a potentially hazardous situation could arise when a patient 11 delays or skips a meal that normally includes an increase or "jump" in basal rate. If the change in basal rate was triggered by the patient 11 indicating the real starting point of a meal, patient safety would be restored because the basal rate would not change until the actual start of the meal.

Figure 3:
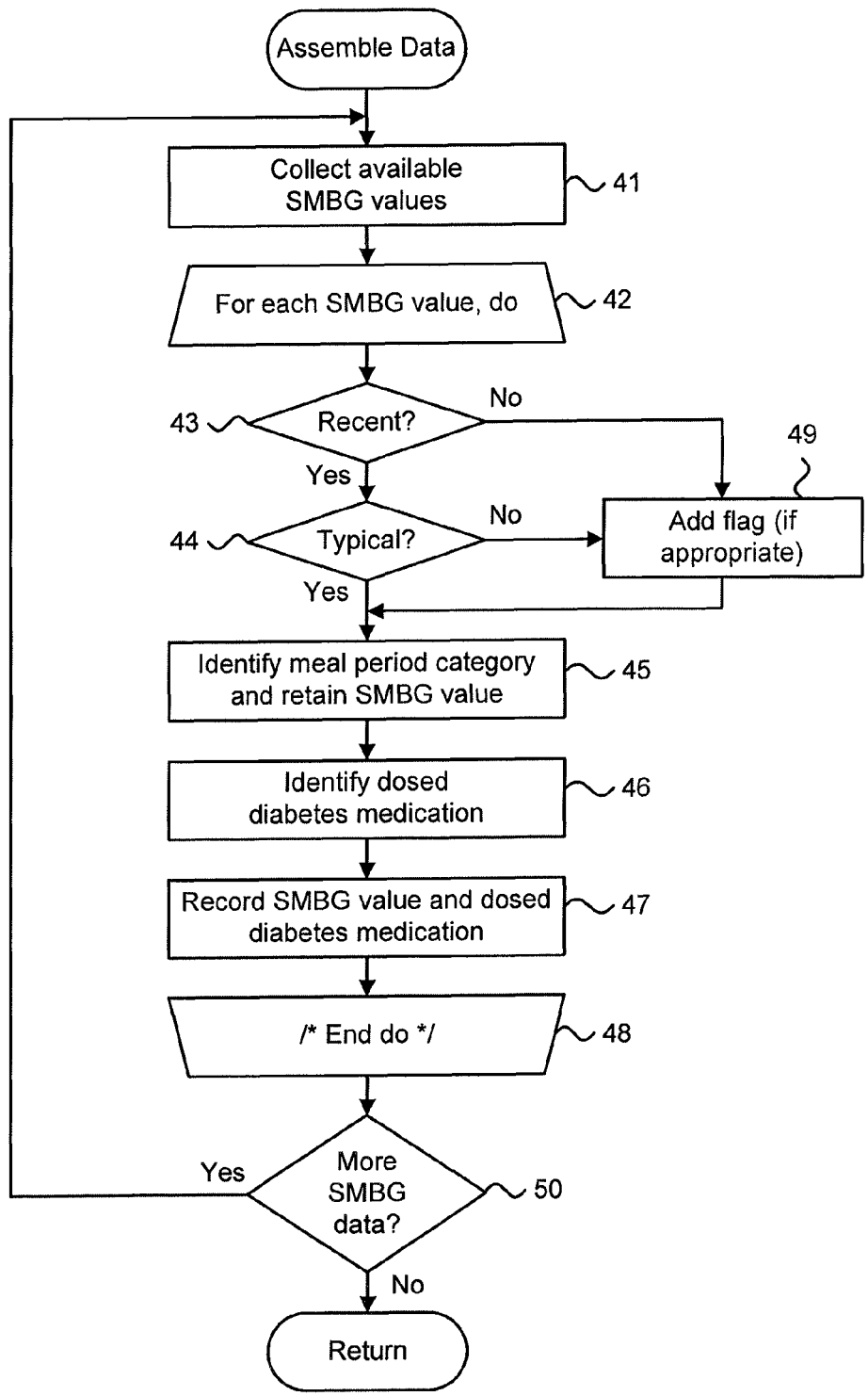
FIG. 3 is a flow diagram showing a routine for assembling meal period data for use in the method of FIG. 2.

The formation of a circadian profile begins with assembling meal period data, which includes both SMBG measurements and any diabetes medications dosed, including insulin and oral agents, for the patient 11 for meal periods occurring over a recent observational time frame, typically from the last seven days, into the database 14 (step 31), as further described infra with reference to FIG. 3. The meal period data is then organized into a circadian profile (step 32), as further described infra with reference to FIG. 4. Meal period data is cumulatively collected from the patient 11 (step 33). Additional data is accepted from the patient 11 and preferably at least two typical measurements of pre-meal and post-meal SMBG are eventually collected for each meal period. Upon completion, the meal period data, including the completed circadian profile, is uploaded from the personal or laptop computer 15 or mobile computing device to the network 21 (step 34) for storage and evaluation in a "cloud" computing infrastructure (step 35), as further described infra with reference to FIG. 5.

Meal periods form a set of categories within which SMBG values and diabetes medication, including insulin and oral agents, are stored and statistically analyzed. FIG. 3 is a flow diagram showing a routine 40 for assembling meal period data for use in the method 30 of FIG. 2. First, the available SMBG values are collected (step 41). In a further embodiment, the SMBG values may be pre-populated and simply verified once the user validates. For instance, wireless-capable glucometers could transmit SMBG readings automatically to populate the patient's database as maintained in cloud storage. Each of the SMBG values is systematically validated (steps 42-48), as follows. To ensure accurate prediction of glycemic outcome, only recent and typical SMBG values are allowed. Recent (step 43) means that the SMBG value was obtained during the seven days preceding the next caregiver consultation. Other time frames are possible, but increasing the window beyond seven days undermines the value and meaningfulness of the SMBG data as reflective of current actual glycemic condition. Typical (step 44) means that each of the SMBG values is without qualifications or exception. For instance, an SMBG measurement taken following a substantial Thanksgiving Day feast would be atypical and would not be representative of the patient's typical diet.

When entering data, the patient 11 has the ability to flag SMBG values (step 49) as not being either recent (step 43) or typical (step 44) either by performing a point-and-click operation with his mouse or other pointing device, or by manually typing comments in an editable comments field in the circadian profile. The patient 11 also identifies the applicable meal period category, for instance, pre-breakfast, and the SMBG value is retained (step 45). The ability to flag atypical SMBG values enables a patient 11 to associate a particular SMBG value with one or more events that can help explain the departure from expected and typical SMBG levels, such as a high or low carbohydrate intake, exercise or physical activity, or stress, as further described below with reference to FIG. 11. These explanatory events can be graded in levels relative to their normal baseline. In a further embodiment, flagged atypical SMBG values can be differentially weighted for use in the determination of expected blood glucose values and predicted errors, as further described infra, discarded or used in any other way.

If the SMBG value is both recent and typical, the patient 11 identifies the applicable meal period category, for instance, pre-breakfast, and the SMBG value is retained (step 45). Data entry can be done all at once, or episodically, as convenient.

As the program 15 can model insulin and most oral (tablet) or injected anti-diabetes drugs, the patient 11 also identifies any diabetes medications, including oral or injected anti-diabetic agents and insulin doses, which were taken or administered about the time that the blood glucose was measured (step 46). Both basal and bolus insulin dosing, plus optionally, the site of insulin injection on the patient's body, are identified. Insulin injection site provides a point of discussion between the caregiver and the patient 11 during consultation in light of the affect that injection site can have on insulin absorption and therefore the rate of glycemic regulation. The SMBG value and the diabetes medication dosing are stored into the database 14 under the meal period category that was identified by the patient 11 (step 47).

The ability to flag atypical SMBG values enables a patient 11 to associate a particular SMBG value with one or more events that can help explain the departure from expected and typical SMBG levels, such as a high or low carbohydrate intake, exercise or physical activity, or stress, as further described below with reference to FIG. 12. These explanatory events can be graded in levels relative to their normal baseline. In a further embodiment, flagged atypical SMBG values can be differentially weighted for use in the determination of expected blood glucose values and predicted errors, as further described infra, discarded or used in any other way.

In one embodiment, only a single type of basal insulin, that is, longer-acting insulin with a physiologic mechanism of action principally spanning one half day to no more than one full day, and a single type of bolus insulin, that is, shorter-acting insulin with a physiologic mechanism of action principally spanning no more than three to eight hours, are accepted into the circadian profile. Other types of longer-acting and short-acting drugs in addition to or in lieu of insulin could also be accepted. However, dosing of different types of insulin having the same temporal mechanism of action, such as multiple simultaneous or overlapping short-acting insulin, is not permitted, as the net affect of arbitrarily combinable multiple insulin dosing is ambiguous and cannot be modeled with sufficient predictive certainty.

In a further embodiment, glucose lowering drugs, including shorter-, intermediate-, and longer-acting classes of anti-diabetes drugs, particularly oral hypoglycemia drugs, are modeled in addition to or in lieu of insulin. These medications include insulin sensitizers, including biguanides and thiazolidinediones; secretagogues, such as sulfonylureas and non-sulfonylurea secretagogues; alpha-glucosidase inhibitors; and peptide analogs, for instance, injectable incretin mimetics, injectable Glucagon-like peptide analogs and agonists, gastric inhibitory peptide analogs, dipeptidyl Peptidase-4 inhibitors, and injectable Amylin analogues. Other types of glucose lowering medications could also be accepted.

Finally, a minimum of two SMBG values per meal period are needed to form a complete circadian profile, one pre-meal measurement and one timed post-meal measurement, which, for statistical purposes, should be repeated a minimum of two times apiece for a total of 16 SMBG values, although more data, up to the maximum possible over a recent time frame, are possible. In one embodiment, a maximum of 56 SMBG values can be accepted, which account for one pre-meal SMBG value for breakfast, lunch, and dinner (three SMBG values) and one timed post-meal period SMBG value also for breakfast, lunch, and dinner (three more SMBG values), also a bedtime and an overnight (two SMBG values), over an entire seven-day week. The patient 11 continues to enter SMBG data (step 50) until all available data up to that time have been entered.

Conventional approaches to diabetes management are often retrospective in that changes in treatment are primarily based on historical, rather than recent, glycemic outcomes. In contrast, a circadian profile, as described herein, shifts the focus to recent indicators of glycemic condition and only for typical meal periods, which enables accurate prediction of short-term blood glucose and A1c outcomes. FIG. 4 is a user interface diagram showing, by way of example, an interactive screen 60 for a circadian profile 61 for use in the system 10 of FIG. 1. The interactive screen 60 is generated by the program 15 for use by both the patient 11 and the caregiver during consultations.

The circadian profile fits within the "three-legged stool" metaphor of clinical diabetes management that focuses on body weight, A1c level and glycemic management. The creation of each circadian profile begins with assembling and organizing SMBG values and diabetes medication, as well as other relevant information that is stored into the database 14. The patient's and caregiver's demographics 62 are entered as an initial step. The remainder of the circadian profile 61 contains patient information that is organized under a series of pre-meal and timed post-meal categories 63. In one embodiment, eight categories 63 of meal periods are defined for breakfast, lunch and dinner: pre- and timed post-meal, pre-bedtime and overnight periods, although other category-based series are possible, including mid-meal periods. Within each category 63, the patient's body weight, SMBG values 64 and their times of measurement are entered, plus any diabetes medication 65 that was taken or administered. In addition, for those patients who are on injections of insulin, the site of injection is also entered, which provides a talking point during patient consultation. Finally, the patient 11 can enter optional comments 66 on lifestyle, including carbohydrate estimate ("CHO"), exercise or physical activity level ("EX"), stress, and so forth. The lifestyle comments are also points of possible discussion with the caregiver. Other patient data can also be collected, like blood pressure and resting heart rate. In addition to allowing each patient's database to be portable and ensuring that their data is virtually unloseable, the storage of each patient's meal period data in the "cloud" allows collaborative online modeling of predictive circadian profiles through social networking, which can be used and shared by the caregiver and patient 11, as well as his support community. FIG. 5 is a flow diagram showing a routine 70 for storing and evaluating uploaded meal period data for use in the method 30 of FIG. 2. The wider availability of the diabetes management data beneficially enlarges the circle of care to include the support community that helps patients in dealing with diabetes on a day-to-day basis. Patients gain access to peer support and encouragement in a virtual community, which mimics a traditional support group setting. Patients can learn from each other's experiences with glucose management, which allows them to avoid similar pitfalls in their own medication or lifestyle management. Patients can also share their circadian profiles, either to request input from the support community on how to improve their glycemic control or as a point of pride to display the circadian profile after successfully achieving glycemic control falling within target range. In addition, patients can form groups within their social network based on friends, coworkers, and individuals with a similar type of diabetes or medication. These social network groups can participate in competitions for achieving outcomes, such as glucose control, A1C targets, elimination of hypoglycemia, and so forth. They can also earn rewards in this virtual community for achieving milestones or outperforming peers.

To safeguard access to a particular patient's data, every user operates within a secure environment (steps 71-77) that begins with validating each user's credentials (step 72) through the DMS 23 (shown in FIG. 1). Only patient data for which the user has received permission to view can be retrieved (step 73). Once retrieved, the patient data can be used to generate glycemic predictions and visualizations. The short-term, typically 7-day, time frame over recent glycemic management provided by the circadian profile has been shown to allow accurate prediction of blood glucose outcomes. As a result, a model of the expected values of near-term blood glucose values and their predicted errors can be created and visualized (step 74), as further described infra with reference to FIG. 6. The visualization identifies those meal periods that are accompanied by a predicted risk of hypoglycemia or occurrence of hyperglycemia, which the caregiver is urged to address with the patient 11 during consultation. In addition, the CG&MT target ranges or, if preferred, the caregiver's targets for the patient 11, can be superimposed over the visualized blood glucose prediction to enable the caregiver to evaluate likely excursions from well-managed glycemic care (step 75), as further described infra with reference to FIG. 7.

Through the visualized glycemic outcome model, incremental suggestions on possible changes to medication dosing can be provided, which the caregiver can interactively explore to evaluate likely near-term affect on the patient 11. The program 15 supports the interactive exploration and modeling of all manner of anti-diabetes drugs, including insulin, other injectable medications and oral agents. As selected by the caregiver, potential changes in medication dosing are visually propagated over the blood glucose prediction (step 76), as further described infra with reference to FIG. 9. Other steps to further the patient consultation are possible, such as reviewing weight control through body mass index calculation and body weight trend analysis.

Figure 6:
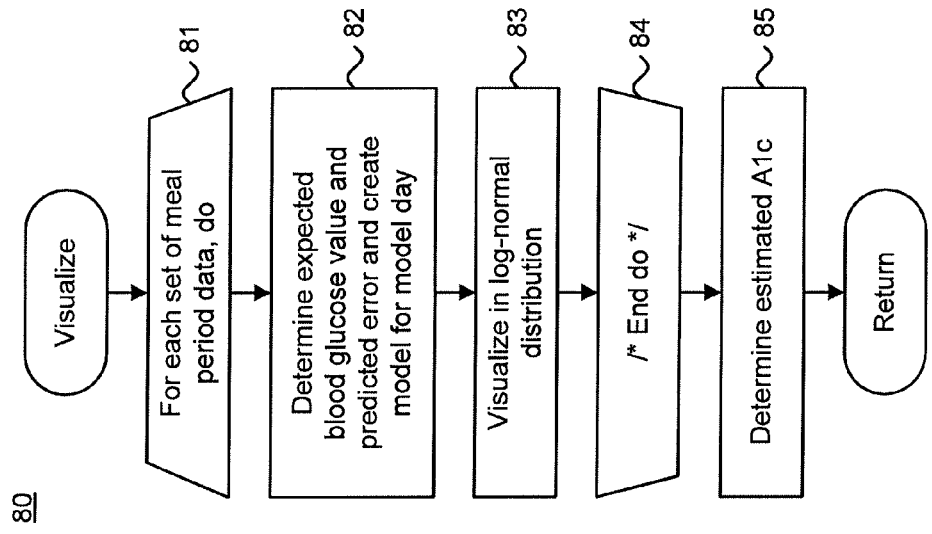
FIG. 6 is a flow diagram showing a routine for visualizing expected blood glucose values and predicted errors for use in the routine of FIG. 5.

The categorization of recent typical SMBG values into a circadian profile enables accurate prediction and modeling of near-term blood glucose and A1c levels. FIG. 6 is a flow diagram showing a routine 80 for visualizing expected blood glucose values and predicted errors for use in the routine 70 of FIG. 5. Each of the sets of meal period data is evaluated and modeled (steps 81-84), as follows. The expected blood glucose value and predicted error for each meal period on the category axis is first determined and a model of the expected blood glucose values and their respective predicted errors by meal periods is created for a model day (step 82). During the statistical determination of the expected blood glucose values and predicted errors, all SMBG values may be treated as having equal weight in terms of their respective influence on the prediction and modeling of near-term blood glucose and A1c levels. In a further embodiment, individual SMBG values can be flagged and differentially weighted based on a weighting criteria, such as used to flag atypical SMBG, as discussed supra, which causes the model to reflect the relative influence of each SMBG value based on its respective weight. Other ways of emphasizing or deemphasizing factors affecting SMBG monitoring are possible.

A seven-day window is used to generate the model. Recall that a replicated minimum of two SMBG values per meal period is preferred, although more data within the seven-day observational time frame are believed to improve accuracy. The statistical methods for performing the near-term blood glucose level prediction has been clinically validated for both efficacy and safety, such as described in A. M. Albisser et al., Home Blood Glucose Prediction: Validation, Safety, and Efficacy Testing in Clinical Diabetes, *Diabetes Tech. Ther.*, Vol. 7, pp. 487-496 (2006); and A. M Albisser et al., Home Blood Glucose Prediction: Clinical Feasibility and Validation in Islet Cell Transplantation Candidates, *Diabetologia*, Vol. 48, pp. 1273-1279 (2005), the disclosures of which are incorporated herein by reference.

Empirically and as scientifically demonstrated supra, when assembled into distinct pre- and timed post-meal categories, SMBG data follows a log-normal distribution. Consequently, the expected blood glucose value and predicted error for each meal period are visualized using a log-normal distribution (step 83), as further described infra with reference to FIG. 8. Statistically, each expected blood glucose value is the geometric mean of the SMBG values stored in the database 14 for the observational time frame and the predicted error is the standard deviation of the geometric mean. When the patient's blood glucose and A1C values are within target range, the type of statistical distribution used in the model becomes less crucial. As a result, in a further embodiment, a standard normal distribution can be used instead of a log-normal distribution. Under the same rationale, still other types of statistical distributions could also be used.

After all of the sets of meal period data have been evaluated and modeled, an A1c estimate is determined (step 85) for inclusion with the visualization. In one embodiment, the patient's A1c is derived from mean SMBG values, such as described in C. L. Rohlfing et al., Defining the Relationship Between Plasma Glucose and HbA(1c): Analysis of Glucose Profiles and HbA(1c) in the Diabetes Control and Complications Trial, *Diabetes Care*, Vol. 25(2), pp. 275-8 (2002), the disclosure of which is incorporated by reference.

Figure 7:
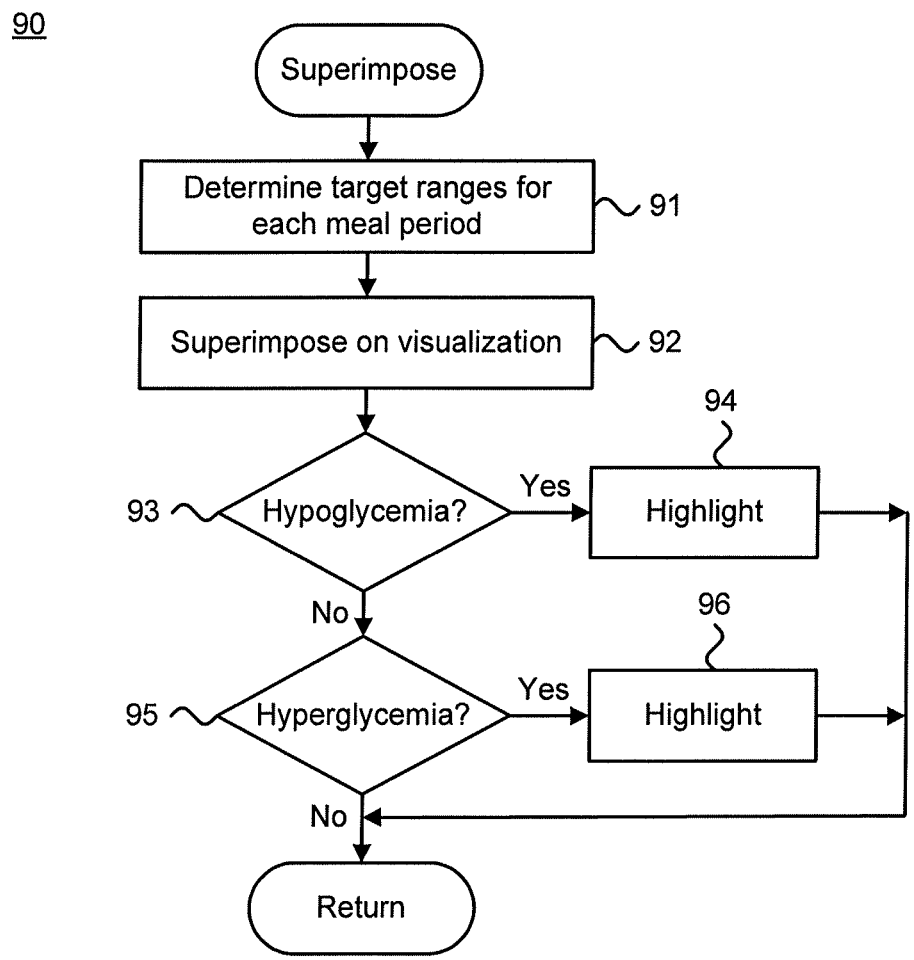
FIG. 7 is a flow diagram showing a routine for superimposing target ranges over the expected blood glucose values and predicted errors for use in the routine of FIG. 5.

With a circadian profile 61 for a diabetic patient 11, a caregiver is able to apply a "treat to target" approach, as presented through a visual display of glucose management data, that focuses on moving the patient's SMBG values into target ranges that represent recognized well-managed glycemic control, as opposed to merely keeping A1c below a certain point. FIG. 7 is a flow diagram showing a routine 90 for superimposing target ranges over the expected blood glucose values and predicted errors for use in the routine 70 of FIG. 5. The one-to-one correspondence between the meal periods in each circadian profile 61 and the CG&MT mandated target ranges enables the expected blood glucose levels and the target ranges to be visualized together.

As an initial step in the approach, the target blood glucose level ranges for each meal period are determined for the diabetes patient 11 (step 91). The target ranges are then visually superimposed over the expected blood glucose levels and the ranges (step 92). The target ranges can either be from the CG&MT or as specified by the caregiver. In one embodiment, different sets of target ranges can be used, including a "default" target range, a gestational diabetes target range (women only) and a target range for use in breaking insulin resistance. The default target range specifies a pre-meal target of 80 mg/dL<SMBG value<140 mg/dL and a post-meal target of 80 mg/dL<SMBG value<180 mg/dL, regardless of whether the meal period is breakfast, lunch or dinner. The gestational target range decreases the pre-meal target range to 60 mg/dL<SMBG value<120 mg/dL. The insulin resistance target range raises the pre-meal target to 120 mg/dL<SMBG value<180 mg/dL, which has the affect of providing the patient 11 with a reason to reduce medication dosing by moving his SMBG values into the (raised) target range, instead of continually increasing medication in a futile attempt to reach the mandated target range. Once the insulin-resistant diabetes patient 11 has achieved the raised insulin resistance breaking target, the default target range can again be approached in steps.

The treat-to-target approach is equally applicable to controlling hyperglycemic occurrence and hypoglycemic risk, where medication must respectively be increased or decreased. The expected blood glucose level in each meal period is respectively compared to hypoglycemic and hyperglycemic thresholds (steps 93 and 95) and, if a risk exists, the meal period is highlighted and a notice is displayed to inform the patient 11 and his caregiver (steps 94 and 96). In one embodiment, a hypoglycemic threshold of 50 mg/dL and a post-meal hyperglycemic threshold of 180 mg/dL are used, where an expected blood glucose level falling outside of either threshold will trigger an appropriate warning. The treat-to-target approach also dovetails well with dietary educational efforts in which the patient 11 is taught to either decrease or increase carbohydrate intake to respectively avoid onset of hyperglycemia or hypoglycemia.

Figure 8:
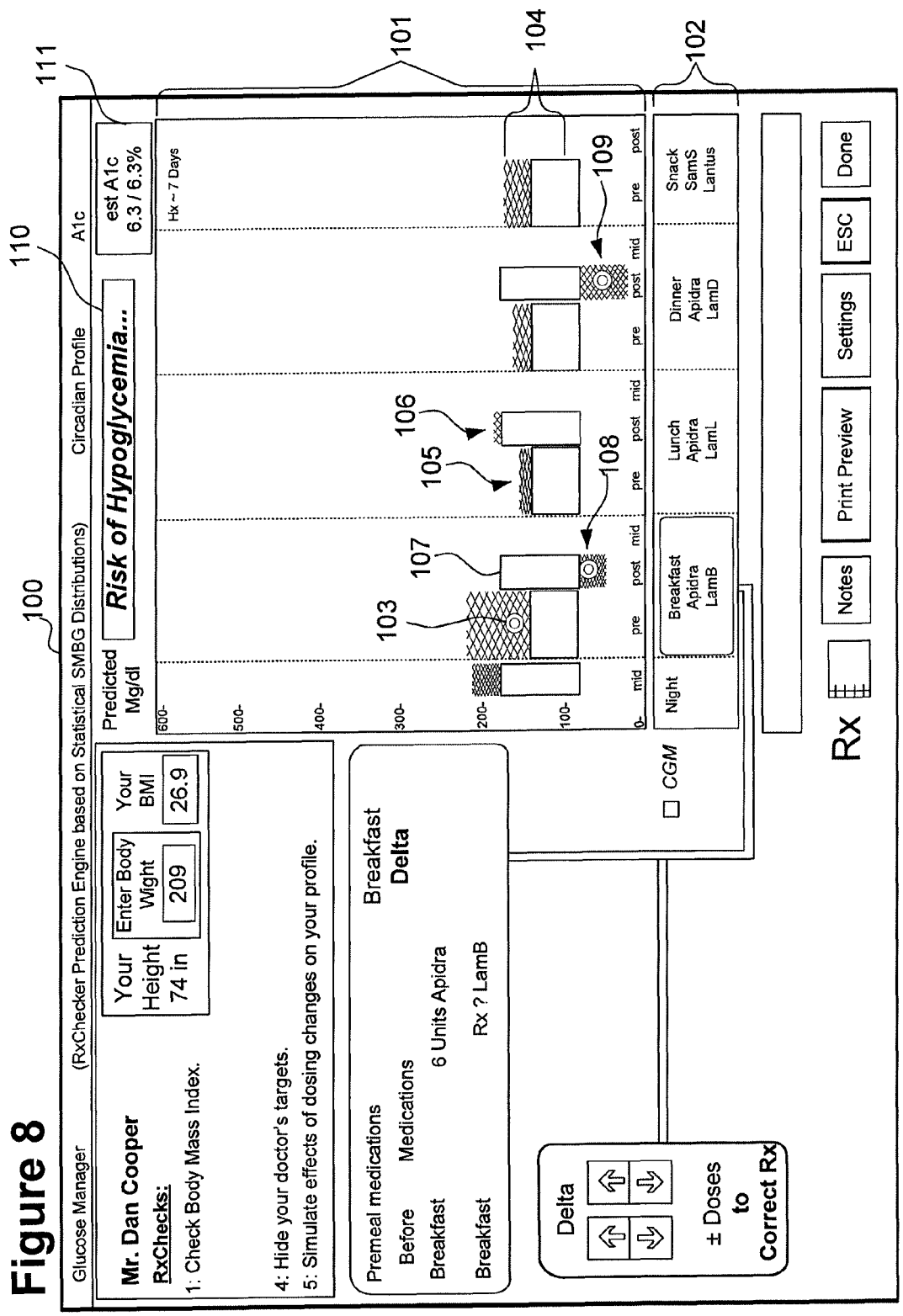
FIG. 8 is a user interface diagram showing, by way of example, an interactive screen for visualizing and evaluating the expected blood glucose values and predicted errors for use in the system of FIG. 1.

The treat-to-target approach is facilitated through a graphical visualization of the model of the expected blood glucose values and predicted errors with mandated target ranges superimposed. FIG. 8 is a user interface diagram showing, by way of example, an interactive screen 100 for visualizing and evaluating the expected blood glucose values and predicted errors for use in the system 10 of FIG. 1. Since the program 15 does not make changes to the patient's course of treatment per se and only provides guidance, the screen 100 can be used by both the patient and the caregiver, as well as other users.

The visualization groups the expected blood glucose values and their respective predicted errors in the model 101 by meal periods 102 for a model day. The model 101 represents the patient's expected blood glucose values 103 and predicted errors 104 before predicted affects of medication dosing increments. Each of the meal periods 102 includes categories 105, 106 for a pre-meal and a timed post-meal expected blood glucose value 103 and a predicted error 104. Due to the log-normal distribution, the predicted error 104 above and below an expected blood glucose value 103 is not symmetric and a wider predicted error 104 appears above each expected blood glucose value 103 than below. The target ranges 107 are superimposed over each of the expected blood glucose values 103. When the probability risk is greater than 5%, or other selectable range, that the expected blood glucose values 108, 109 will fall below the hypoglycemic threshold, the risk is flagged with a warning 110 displayed to the user. As a result, those meal periods where predicted blood glucose values may fall out of target range can be readily identified by the caregiver and patient alike. Finally, the estimated A1c 111 derived from mean SMBG values is displayed.

Figure 9:
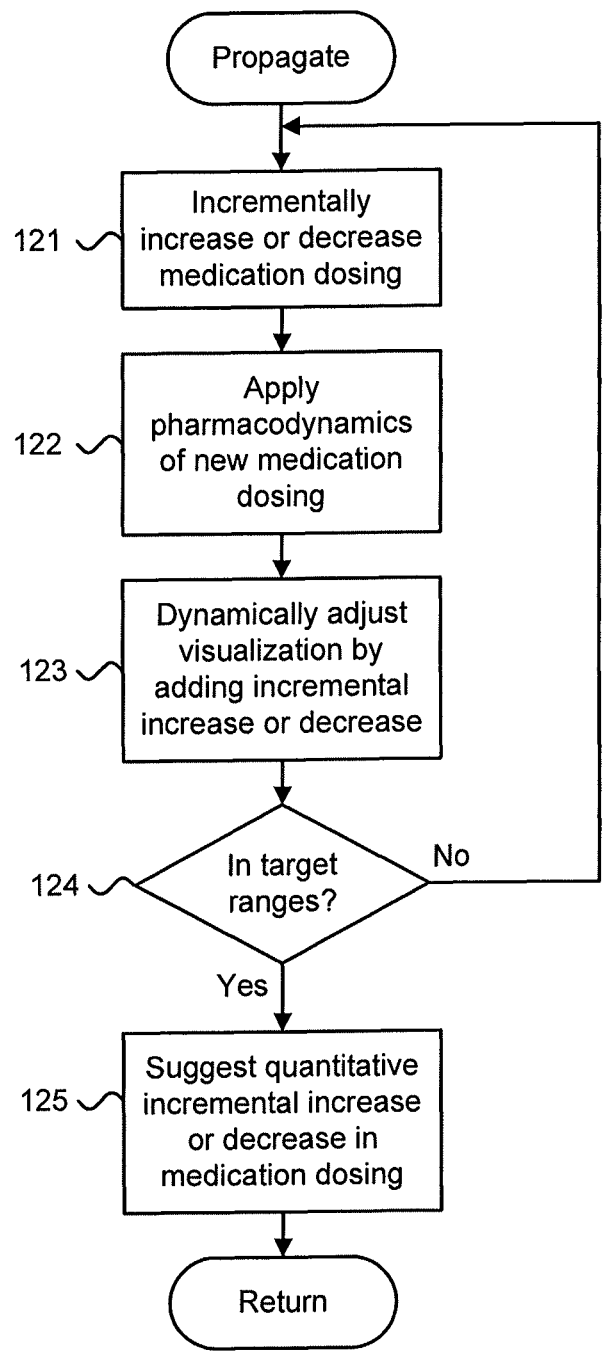
FIG. 9 is a flow diagram showing a routine for propagating an incremental change in medication dosing for use in the routine of FIG. 5.

The visualization of the expected blood glucose values and predicted errors, and target ranges provides a starting point for the caregiver to begin working with the patient 11. Changes to diabetes medication, including insulin and oral agents, may be necessary to move the SMBG values into target range. FIG. 9 is a flow diagram showing a routine 120 for propagating an incremental change in medication dosing for use in the routine 70 of FIG. 5. The expected glucose values, as modified by the pharmacodynamics of any medication dosing changes contemplated for the patient 11, enable the program 15 to suggest quantitative changes to medication dosing for caregiver or patient 11 consideration. The program 15 can also generate qualitative feedback. Generating quantitative feedback provides a closed-loop treatment model. For safety, allowable incremental changes in medication dosing are limited in amount to achieve the targets more slowly, but safely, and without the risk of limit cycling. However, to accommodate the slower physiological response of these smaller incremental changes, the patient 11 has to measure SMBG more often, up to six times per day, than with a qualitative approach that works with fewer SMBG values.

The amount of change in medication dosing, based on the diabetes medications already identified by the patient 11, can be determined by either incrementally increasing or decreasing the amount of the dosed medication in the model 101 (step 121). The pharmacodynamics of the diabetes medication is applied in proportion to the incremental change in dosing, as incrementally increased or decreased (step 122), and the visualization is dynamically adjusted by adding the incremental increase or decrease in blood glucose level to the expected blood glucose values 103 (step 123). The program 15 uses the pharmacodynamics of the diabetes medications to model the affect on the expected values of near-term blood glucose values and their predicted errors. Drug manufacturers formulate their drugs, so that an incremental change in dosing, amounting to the smallest dosing unit, such as a half tablet of an oral medication of the lowest strength or one IU of an injectable medication, produces a glucose lowering effect similar to all the other anti-diabetes drugs in its class. This "normalization" is used to avoid having their drug require different dosing profiles when compared to comparable drugs offered by their competitors, where, for instance, one manufacturer's medication may require three oral tablets while a competitor's medication only requires a single oral tablet.

The normalization of comparable anti-diabetes medications is reflected in the visualization, which allows a user to change medication dosing incrementally (steps 121-123) until the expected blood glucose values move into the target ranges (step 124). The pharmacodynamics allow one "click" on the user interface to reflect a similar glucose lowering affect for all anti-diabetes drugs in the same class, although the pharmacodynamics of different drug classes are applied in such a way as to normalize the area under the response curves to reflect the total drug administered. As a result, longer-acting drugs have a lower peak, but last longer to keep the area under the blood glucose curve similar to the same amount of a shorter-acting drug, which has a higher peak and short duration of action. That amount of incremental increase or decrease in the dosed medication is then presented to the caregiver as an incremental suggested change in medication dosing (step 125). The qualitative scale is slight, moderate, or significant, although in a further embodiment, this scale can also be expressed quantitatively. Specifically, the program 15 scales six left whole-clicks or twelve right half-clicks to span the range from slight qualifiers (+), to moderate qualifiers (++), and finally to significant qualifiers (+++) for all dosage increments, or decrements, which allows "clicks" to be quantified into usable measures of dosing, such as half oral tables or IUs of insulin. In addition, the program 15 provides a mechanism for simply "accepting" or documenting medication changes, such that those changes that are pre-populated when the patient 11 enters SMBG readings and verifies the doses taken.

In a further embodiment, the circadian profile and incremental increase or decrease in the dosed medication could be uploaded back into the patient's personal database 14 on his personal or laptop computer 13, mobile computing device, portable media device 12, glucometer 17 or other type of portable blood glucose testing device with onboard data collection capabilities, as applicable. The circadian profile and incremental change in the dosed medication are uploaded, depending upon whether the glucometer 17 is used as a dosing treatment controller, where the incremental changes are uploaded, or a regimen guidance tool, in which the incremental changes are maintained separately and offline from the glucometer 17. The decision on how to use the glucometer 17 in diabetes management and uploading the incremental changes into the onboard database turns on whether such usage is thought of as being inside or outside the treatment arc that connects the output of the glucometer 17 to the "tip of the needle," that is, the drug delivery device. The incremental changes would be uploaded back on to the glucometer 17 if the onboard database is intended to be portable and the patient 11 intends to run the program 15 on any personal or laptop computer 13 or mobile computing device without the benefit of a virtualized database provided through a "cloud" computing infrastructure. However, incremental change uploading can potentially become cumbersome if the patient 11 has more than one glucometer 17 actively in use, such as at home and at work, and keeping the databases on each of those devices current could become a logistical challenge to the patient 11 and his caregiver.

In a still further embodiment, a caregiver can model proposed changes to medication dosing and, through the cloud storage infrastructure, feed the results back to the patient's personal or laptop computer 13, mobile computing device, portable media device 12, glucometer 17 or other type of portable blood glucose testing device with onboard data collection capabilities, as applicable. In addition, manufacturers of glucose meters and glucose sensing strips that are able to monitor their devices can also be participants to the caregiving process. These manufacturers can provide continued calibration and other performance metrics that will assure quality, accuracy, and safety in their measuring devices and signal an unsafe or unreliable status, which would flag a reading as possibly atypical or unreliable.

Figure 10:
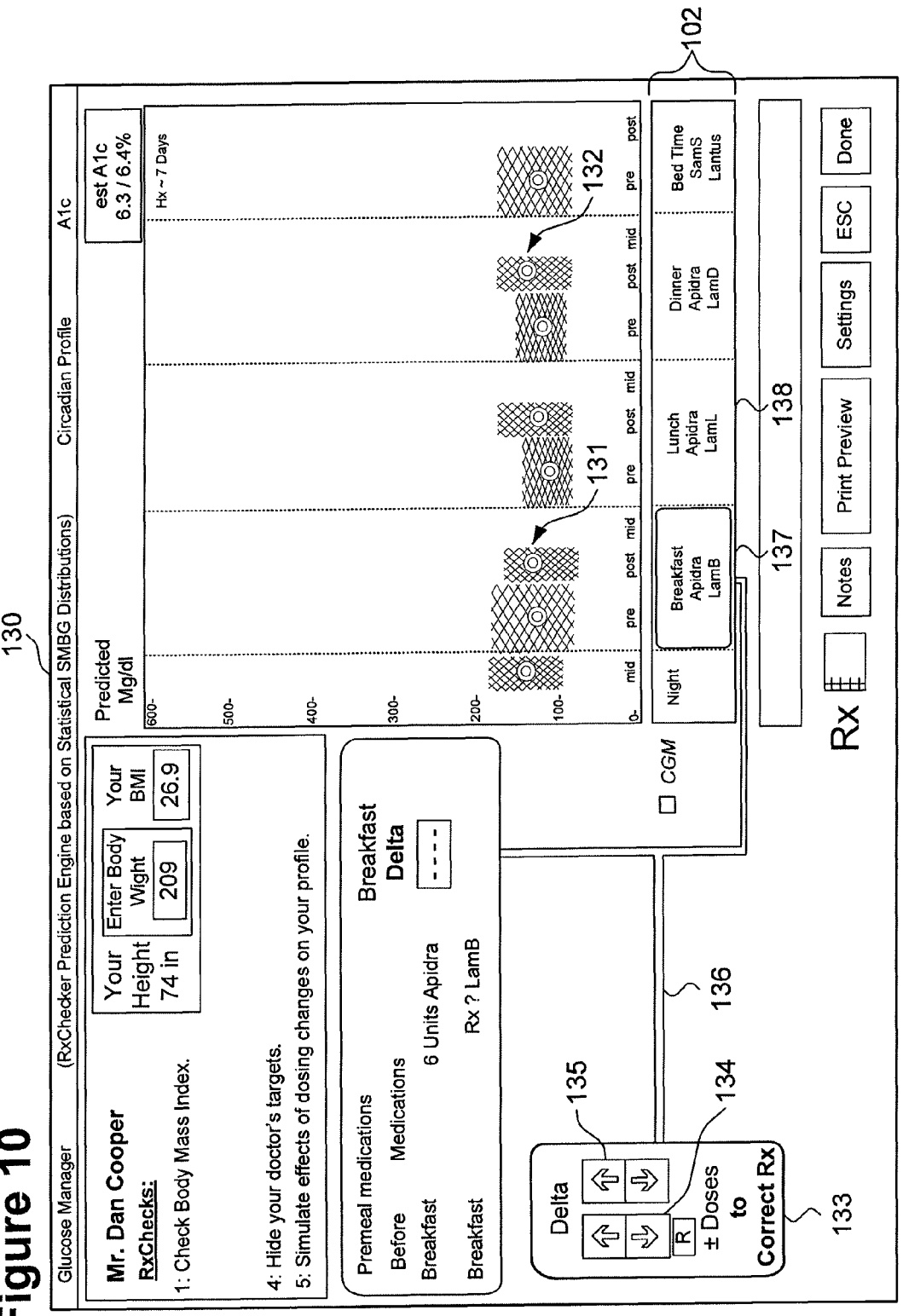
FIGS. 10 and 11 are user interface diagrams showing, by way of example, interactive screens for modeling incremental changes in medication dosing for use in the system of FIG. 1 respectively before and after superimposing the target ranges.
Figure 11:
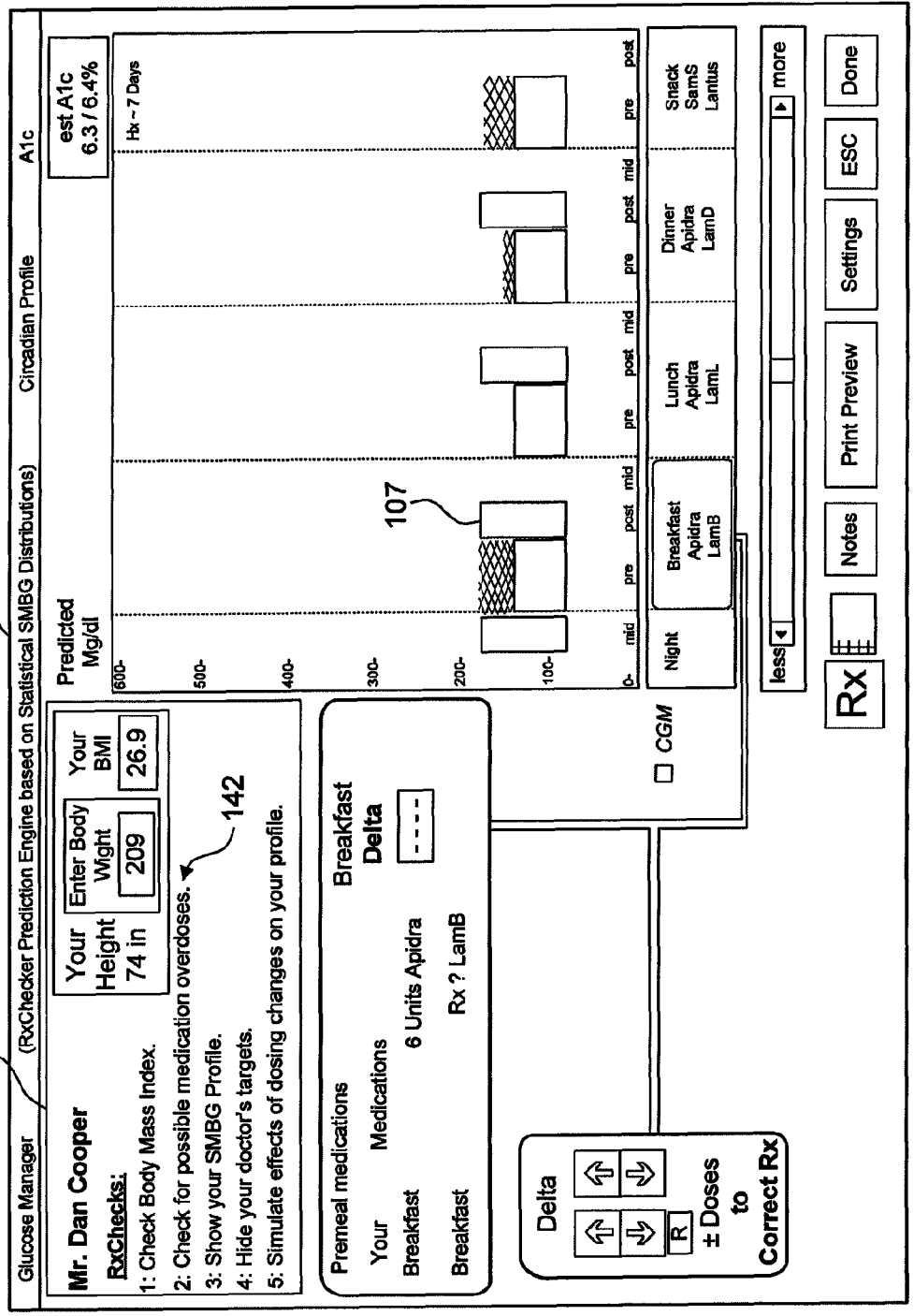

Throughout exploration of potential medication dosing changes, including insulin and oral agents, the possible affect of any suggested change, or other amount of change in medication dosing desired, is added to the visualization by dynamically adjusting the expected glucose values based on the relative pharmacodynamics of the new medication dosing change. FIGS. 10 and 11 are user interface diagrams showing, by way of example, interactive screens 130, 140 for modeling incremental changes in medication dosing for use in the system 10 of FIG. 1 respectively, before and after superimposing the target ranges. Referring first to FIG. 10, with the new medication dosing, the two expected blood glucose values 131, 132 that formerly risked hypoglycemia at a 5%, or greater probability are now safely raised and the risk of hypoglycemia has been removed. In addition to the actual medications described (Apidra and Lantus), the fields in the descriptor bar for meal periods 102 include placeholders at the breakfast, lunch and dinner meal periods for longer-acting (insulin) medications ("LamB," "LamL," "LamD") and at only the bedtime "meal" period for shorter-acting (insulin) medication ("SamS").

Changes to the dosed medications, whether insulin or oral agents, can be explored by the user through a control panel 133 (labeled "±Doses to Correct Rx"). Within the control panel 133, controls 134, 135 under the label "Delta" respectively allow the user to explore incrementally increasing or decreasing the shorter-acting and longer-acting medications for a meal period 102, as indicated by a connector line 136. The sub-control button (labeled 'R') serves as a shortcut to reset any explored increments back to zero. Here, the breakfast meal period 137 is selected with the shorter-acting medication set to Apidra and the longer-acting medication set to LamB, which is, an as-yet unspecified, longer acting medication at B. To explore the impact of medication dosing changes during other meal periods 102, for instance, the lunch meal period 138, the user selects the area labeled "Lunch," upon which the lunch meal period 138 is connected by the connector line 136 to the control panel 133 and the breakfast meal period 137 is deselected.

In one embodiment, the change in insulin dosing can be presented in standard dosage IUs (International Units), in increments of tenths of an IU, where the scaling is rationalized for the patient's delivery device. For instance, hypodermic syringes have a scale that depends on their full volume, whereas insulin injection pens dose in increments of 1 IU or 2 IU per click. Insulin pumps are capable of doing in increments of 0.1 IU. However, in practice, insulin dosing can be course when the dose is over 10 IU and finer for infants whose dose could be ~1 IU, such as 1.5 IU or 0.5 IU. In suggesting the final change in insulin dosing to the patient 11 or caregiver, the quantitative dose suggestion could follow a conversion of clicks for an insulin injection pen or some other individualized scaling factor that depends on the size of the total daily dose. Quantifying the clicks to tablets conversion could be by 0.5 tablets up to a maximum of 1 to 3 tablets, or limited by the maximum meal and daily allowable amounts.

The expected blood glucose value 103 and predicted error 104 for each meal period 102 are adjusted for the pharmacodynamics of the changes to the diabetes medication being explored. Typically, the pharmacodynamics follow the dose-response characteristic. The pharmacodynamics define the effect of the drugs, that is, the patient's diabetes medication, on blood glucose. The pharmacodynamics of each type of drug is available from the manufacturer. Beginning with the meal period at which the diabetes medication change was administered, the pharmacodynamics are used to raise or lower the expected level of blood glucose in the visualization until the propagated pharmacodynamics are fully exhausted. Depending upon the particular drug's pharmacodynamics, the expected blood glucose levels in a sequence of several adjacent meal periods may be affected. For instance, insulin glargine taken as a basal dose is long-acting and the pharmacodynamics will affect meal periods for several days, although the insulin's ability to lower blood glucose level after the first 24 hours is significantly diminished. As well, insulin taken as a pre-meal bolus dose is short-acting, yet the pharmacodynamics may well equally propagate for an entire day, albeit of relatively small continuing blood glucose level-lowering affect. However, assuming a linear model, the cumulative pharmacodynamics of all of the basal doses and each of the bolus doses taken throughout the observational time frame may nevertheless lower the expected blood glucose level at any given meal period more than a single bolus dose would if taken at that same meal period in isolation from any other insulin doses.

Following (or during) the exploration of changes to the medication dosing, including insulin or oral agents, the target ranges 107 can be superimposed to provide visual guidance as to whether the new medication dosing will satisfactorily move the expected blood glucose values 103 into the mandated targets and avoid both the risk of hypoglycemia and occurrence of hyperglycemia. Referring next to FIG. 11, the target ranges 107 have been superimposed above the expected blood glucose values 103 and predicted errors 104. All of the patient's expected blood glucose values 103 are within target and reflect ideal glycemic control. In addition, the caregiver is able to also ensure proper dosing of medications through a set of prescription checkers steps ("RxChecks") 141 that includes a control 142 to "Check for possible medication overdoses," which checks that medication is dosed within safe limits at each meal period and for the entire day. Other types of prescription checks and safeguards are possible.

Atypical SMBG values can also serve to guide the medication dosing adjustment processes. FIG. 12 is a user interface diagram showing, by way of example, an interactive screen 150 for a circadian profile for use in a further embodiment of the system 10 of FIG. 1. The SMBG values 151 and their times of measurement are entered along with an explanation 142 that flags an atypical SMBG value for the lunch meal period. Other labels within the various interactive screens, such as the label accompanying RxChecks steps 141 (shown in FIG. 11), can be highlighted to call attention to unusual events that may lead to atypical SMBG data. Atypical or "unusual" events touch on aspects of the patient's diet, exercise, physical activity, stress, and similar often unavoidable outcomes of activities of daily living, for example, eating an atypical amount of carbohydrates (either more or less than normal, as happens on Thanksgiving Day) without a matching correction bolus, experiencing more or less stress than usual, or engaging in an unusual amount of exercise or physical activity.

In one embodiment, a flagged event triggers the display of a notice to a tooltip associated with the associated post- and mid-meal glucose ranges, that is, "After L" and "Mid L-D." Here, the notice would say, for instance, "Unusual±CHO or unusual activity in this MP may distort this prediction." Similarly, for the following pre-meal glucose range in the following meal period, that is, "Pre D," the notice would say, for instance, "Preceding unusual CHO or unusual activity may distort this prediction." Also, as a further guide in deciding whether to accept or ignore a potentially atypical expected blood glucose value and its range, a tooltip can also be associated with the low end of the predicted range 108 (shown in FIG. 8) for a meal period category, such as "Before L," that includes the acceptable SMBG reading in the range for that meal category. This tooltip notice can be helpful in understanding why a warning about a factitious risk of hypoglycemia that arises from an outlying hyperglycemia event can safely be ignored. Other types and triggers of notice are possible.

While the invention has been particularly shown and described as referenced to the embodiments thereof, those skilled in the art will understand that the foregoing and other changes in form and detail may be made therein without departing from the spirit and scope of the invention.

What is claimed is:

1. A computer-implemented method for improving glucose management through cloud-based modeling of circadian profiles, comprising the steps of:
   defining a plurality of meal periods that each occur each day at a set time;
   building a circadian profile for a diabetic patient, comprising the steps of:
      choosing an observational time frame for the circadian profile comprising a plurality of days that have occurred recently;
      storing online at least two sets of pre- and post-meal period data that comprise blood glucose levels and doses of diabetes medication that were respectively taken during each of the meal periods for which the blood glucose levels were recorded in a cloud computing infrastructure; and
   creating a model of glucose management for the diabetic patient over the cloud computing infrastructure, comprising:
      validating access to the circadian profile;
      estimating expected blood glucose values and their predicted errors at each of the meal periods occurring each day in the modeling period from the blood glucose levels in each data in the validated circadian profile that respectively occur at the same set times;
      visualizing the expected blood glucose values and their predicted errors over time for each meal period occurring each day in the modeling period in a log-normal distribution;
      determining target ranges for blood glucose at each of the meal periods occurring each day in the modeling period and superimposing the target ranges over the expected blood glucose values for each meal period occurring each day in the modeling period in the log-normal distribution; and
      selecting one of the meal periods that occurs on one of the days in the modeling period and modeling a change in the dose of the diabetes medication for the selected meal period, comprising the steps of:
         obtaining a dose-response characteristic comprising a blood glucose lowering effect over time for the modeled change in the dose of the diabetes medication, wherein the blood glucose lowering effect has been normalized with blood glucose lowering effects of diabetes medications based on the same change in the dose;
         propagating the normalized blood glucose lowering effect over time for the modeled change in the dose of the diabetes medication to the expected blood glucose values, beginning with the selected meal period and continuing with each of the meal periods occurring subsequently in the modeling period, the normalized blood glucose lowering effect being adjusted in proportion to the set time of each subsequent meal period until the normalized blood glucose lowering effect is exhausted; and
         visualizing the expected blood glucose values as propagated and their predicted errors in the log-normal distribution,
   wherein the steps are performed on a suitably-programmed computer.

2. A method according to claim 1, further comprising the steps of:
   reading the blood glucose level on a test strip provided to a glucose meter by the diabetic patient for each of the meal periods;
   identifying the doses of the diabetes medication, which were respectively taken during each of the meal period as the readings of the blood glucose levels; and
   storing the blood glucose level and the doses of the diabetes medication into the circadian profile in the data for each of the meal periods.

3. A method according to claim 1, further comprising the steps of:
   modeling an incremental change in the dose of the diabetes medication for the selected meal period;
   applying the normalized blood glucose lowering effect of the diabetes medication in proportion to the dose as incrementally changed until the expected blood glucose values in the log-normal distribution move into the target ranges; and
   providing the incrementally changed dose of the diabetes medication as a suggested incremental dosing change.

4. A method according to claim 1, further comprising the steps of:
   defining a threshold of hypoglycemic risk expressed as a blood glucose value; and
   identifying each of the expected blood glucose values in the log-normal distribution exhibiting a risk of falling below the hypoglycemic risk threshold.

5. A method according to claim 1, further comprising the steps of:

defining a threshold of hyperglycemic occurrence expressed as a blood glucose value; and identifying each of the expected blood glucose values in the log-normal distribution exhibiting a risk of rising above the hyperglycemic occurrence threshold.

6. A method according to claim 1, further comprising the step of:

defining the meal periods as comprising, within each day, breakfast, lunch, dinner, and bedtime meal periods.

7. A method according to claim 1, further comprising the step of:

deriving the target ranges for the blood glucose levels from high and low blood glucose values as published in consensus practice guidelines or as specified by a caregiver of the diabetic patient.

8. A method according to claim 1, further comprising the step of:

modeling the diabetes medication as no more than one shorter-acting drug, which comprises a physiologic mechanism of action principally spanning no more than three to eight hours, and one longer-acting drug, which comprises a physiologic mechanism of action principally spanning one half day to no more than one full day.

9. A method according to claim 1, further comprising the step of:

modeling the diabetes medication as a glucose lowering medication taken by the diabetic patient either in addition to or in lieu of insulin.

10. A method according to claim 1, further comprising the step of:

deriving expected glycated hemoglobin from a mean of the readings of the blood glucose levels during the recent observational time frame.

11. A method according to claim 1, further comprising the step of:

collectively adjusting the target ranges for the blood glucose levels at each of the meal periods occurring each day in the modeling period upward or downward based on a physiological condition specific to the diabetic patient.

12. A method according to claim 1, further comprising the steps of:

including a body weight of the diabetic patient in the circadian profile; and performing a trend analysis of the body weight over any preceding observational time frames.

13. A non-transitory computer readable storage medium storing code for executing on a computer system to perform the method according to claim 1.

14. A computer-implemented system for managing diabetes through cloud computing with circadian profiles, comprising:

an electronically-stored database maintained in a cloud computing infrastructure and comprising a plurality of records, each record comprising a circadian profile, comprising:

a plurality of meal period categories that each occur each day at a set time and divide each circadian profile into the meal period categories;

an observational time frame comprising a plurality of days that have occurred recently;

at least two of typical measurements of pre-meal and post-meal self-measured blood glucose that were recorded at each of the meal period categories that occurred each day in the observational time frame; and doses of diabetes medication that were respectively taken during each of the meal period categories for which the blood glucose measurements were recorded; and an executable application configured to model glucose management, comprising:

a validation module configured to validate access to the circadian profiles through the cloud computing environment;

a collection module configured to collect the blood glucose measurements, upon validation, along a category axis comprising each of the meal period categories;

a statistical engine configured to determine expected blood glucose values and their predicted errors at each of the meal period categories occurring each day in the modeling period from the blood glucose measurements based on the meal period categories on the category axes in the circadian profile that respectively occur at the same set times and to visualize the expected blood glucose values and their predicted errors over time for a each meal period category occurring each day in the modeling period in a log-normal distribution; and a change modeling module configured to select one of the meal period categories that occurs on one of the days in the modeling period and to model a change in the dose of the diabetes medication for the selected meal period category, comprising:

a dose-response characteristic module configured to obtain a dose-response characteristic comprising a blood glucose lowering effect over time for the modeled change in the dose of the diabetes medication, wherein the blood glucose lowering effect has been normalized with blood glucose lowering effects of diabetes medications based on the same change in the dose;

a dosing module configured to propagate the normalized blood glucose lowering effect for the modeled change in the dose of the diabetes medication to the expected blood glucose values, beginning with the selected meal period category and continuing with each of the meal period categories occurring subsequently in the modeling period, the normalized blood glucose lowering effect being adjusted in proportion to the set time of each subsequent meal period category until the normalized blood glucose lowering effect is exhausted; and an visualization module configured to visualize the expected blood glucose values as propagated and their predicted errors in the log-normal distribution.

15. A system according to claim 14, further comprising:

target ranges stored in the database for the expected blood glucose values at each of the meal period categories occurring each day in the modeling period in the log-normal distribution; and a target module configured to superimpose the target ranges over the expected blood glucose values for each meal period category occurring each day in the modeling period in the log-normal distribution.

16. A system according to claim 15, further comprising:

an incremental dosing submodule configured to model an incremental and quantitative change in the dose of the diabetes medication for the selected meal period category, to adjust the expected blood glucose values and their predicted errors in the log-normal distribution based on the normalized blood glucose lowering effect of the diabetes medication in proportion to the dose as incrementally quantitatively changed until the expected blood glucose values in the log-normal distribution move into the target ranges, and to suggest the incrementally quantitatively changed dose of the diabetes medication.

17. A system according to claim 14, further comprising:
a threshold of at least one of hypoglycemic risk and hyperglycemic occurrence, which are both expressed as blood glucose values stored in the database; and
a warning module configured to identify each of the expected blood glucose values in the log-normal distribution exhibiting either a risk of falling below the hypoglycemic risk threshold or rising above the hyperglycemic occurrence threshold.

18. A computer-implemented method for managing diabetes through cloud computing with circadian profiles, comprising the steps of:
structuring a database comprising a plurality of records, each record comprising a circadian profile, comprising:
defining a plurality of meal period categories that each occur each day at a set time and dividing each circadian profile into the meal period categories;
choosing an observational time frame for the circadian profile comprising a plurality of days that have occurred recently;
storing at least two of typical measurements of pre-meal and post-meal self-measured blood glucose that were recorded at each of the meal period categories that occurred each day in the observational time frame;
identifying doses of diabetes medication that were respectively taken during each of the meal period categories for which the blood glucose measurements were recorded; and
maintaining the database in a cloud computing infrastructure; and
modeling glucose management, comprising:
validating access to the circadian profiles through the cloud computing environment;
defining a modeling period comprising a plurality of days, which each comprise the same plurality of the meal period categories that occurred each day in the observational time frame;
upon validation, collecting the blood glucose measurements along a category axis comprising each of the meal period categories;
determining expected blood glucose values and their predicted errors at each of the meal period categories occurring each day in the modeling period from the blood glucose measurements based on the meal period categories on the category axes in the circadian profile that respectively occur at the same set times and visualizing the expected blood glucose values and their predicted errors over time for each meal period category occurring each day in the modeling period in a log-normal distribution; and
selecting one of the meal period categories that occurs on one of the days in the modeling period and modeling a change in the dose of the diabetes medication for the selected meal period category, comprising:
obtaining a dose-response characteristic comprising a blood glucose lowering effect over time for the modeled change in the dose of the diabetes medication, wherein the blood glucose lowering effect has been normalized with blood glucose lowering effects of diabetes medications based on the same change in the dose;
propagating the normalized blood glucose lowering effect for the modeled change in the dose of the diabetes medication to the expected blood glucose values, beginning with the selected meal period category and continuing with each of the meal period categories occurring subsequently in the modeling period, the normalized blood glucose lowering effect being adjusted in proportion to the set time of each subsequent meal period category until the normalized blood glucose lowering effect is exhausted; and
visualizing the expected blood glucose values as propagated and their predicted errors in the log-normal distribution,
wherein the steps are performed on a suitably-programmed computer.

19. A method according to claim 18, further comprising the steps of:
determining target ranges for the expected blood glucose values at each of the meal period categories occurring each day in the modeling period; and
superimposing the target ranges over the expected blood glucose values for each meal period category occurring each day in the modeling period in the log-normal distribution.

20. A method according to claim 19, further comprising the steps of:
modeling an incremental and quantitative change in the dose of the diabetes medication for the selected meal period category;
adjusting the expected blood glucose values and their predicted errors in the log-normal distribution based on the normalized blood glucose lowering effect of the diabetes medication in proportion to the dose as incrementally quantitatively changed until the expected blood glucose values in the log-normal distribution move into the target ranges; and
suggesting the incrementally quantitatively changed dose of the diabetes medication.

21. A method according to claim 18, further comprising the steps of:
defining a threshold of at least one of hypoglycemic risk and hyperglycemic occurrence, which are both expressed as blood glucose values; and
identifying each of the expected blood glucose values in the log-normal distribution exhibiting either a risk of falling below the hypoglycemic risk threshold or rising above the hyperglycemic occurrence threshold.

22. A non-transitory computer readable storage medium storing code for executing on a computer system to perform the method according to claim 18.

* * * * *